(12) United States Patent
Salvati et al.

(10) Patent No.: US 8,216,305 B2
(45) Date of Patent: Jul. 10, 2012

(54) SYSTEMS AND METHODS FOR IMPLANTING AND EXAMINING INTRAOCULAR LENS

(76) Inventors: Stefano Salvati, Rome (IT); Cesare Tanassi, Susegana (IT); Gianluigi Meneghini, Selvazzano Dentro (IT); Renato Frison, Chions (IT); Walter Zanette, San Fior (IT)

( * ) Notice: Subject to any disclaimer, the term of this patent is extended or adjusted under 35 U.S.C. 154(b) by 0 days.

(21) Appl. No.: 12/971,910

(22) Filed: Dec. 17, 2010

(65) Prior Publication Data
US 2011/0087324 A1 Apr. 14, 2011

Related U.S. Application Data

(63) Continuation of application No. 12/569,849, filed on Sep. 29, 2009, now Pat. No. 7,878,655.

(60) Provisional application No. 61/194,721, filed on Sep. 29, 2008.

(51) Int. Cl.
*A61F 2/16* (2006.01)
(52) U.S. Cl. ..................................... 623/6.11
(58) Field of Classification Search ............... 623/6.11, 623/5.11, 4.1
See application file for complete search history.

(56) References Cited

U.S. PATENT DOCUMENTS

| | | | |
|---|---|---|---|
| 4,932,968 A * | 6/1990 | Caldwell et al. | 623/6.37 |
| 7,455,407 B2 | 11/2008 | Neal et al. | |
| 2003/0107706 A1 | 6/2003 | Rubinstein et al. | |
| 2010/0134760 A1 | 6/2010 | Salvati et al. | |

FOREIGN PATENT DOCUMENTS

| | | |
|---|---|---|
| EP | 1683474 | 7/2006 |
| WO | WO 02/088830 | 11/2002 |
| WO | WO 03/022137 | 3/2003 |
| WO | WO 2006/053216 | 5/2006 |
| WO | WO 2009/081286 | 7/2009 |
| WO | WO 2010/035139 | 4/2010 |

OTHER PUBLICATIONS

PCT International Application No. PCT/IB2009/007130 filed Sep. 29, 2009 in the name of Salvati et al, International Search Report and Written Opinion mailed on Aug. 4, 2010.
PCT International Application No. PCT/IB2009/007130 filed Sep. 29, 2009 in the name of Salvati et al, Invitation to Pay Additional Fees mailed on May 6, 2010.
U.S. Appl. No. 12/569,849, filed Sep. 29, 2009 in the name of Salvati et al., Notice of Allowance mailed Aug. 30, 2010.
U.S. Appl. No. 12/569,849, filed Sep. 29, 2009 in the name of Salvati et al., Notice of Allowance mailed Sep. 30, 2010.
US 7,780,728, 08/2010, Hong et al. (withdrawn)

* cited by examiner

*Primary Examiner* — Hung Dang
(74) *Attorney, Agent, or Firm* — Levine Bagade Han LLP

(57) ABSTRACT

Systems and methods for designing and implanting a customized intra-ocular lens (IOL) is disclosed. In one embodiment, a system includes an eye analysis module that analyzes a patient's eye and generates biometric information relating to the eye. The system also includes eye modeling and optimization modules to generate an optimized IOL model based upon the biometric information and other inputted parameters representative of patient preferences. The system further includes a manufacturing module configured manufacture the customized IOL based on the optimized IOL model. In addition, the system can include an intra-operative real time analyzer configured to measure and display topography and aberrometry information related to a patient's eye for assisting in proper implantation of the IOL.

6 Claims, 24 Drawing Sheets

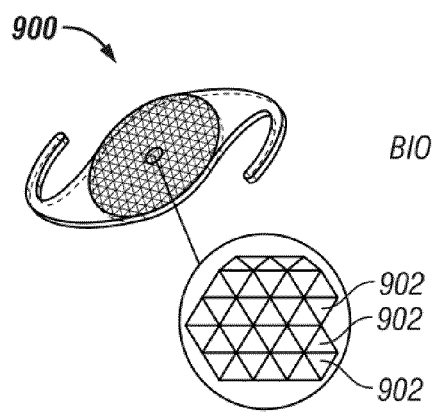
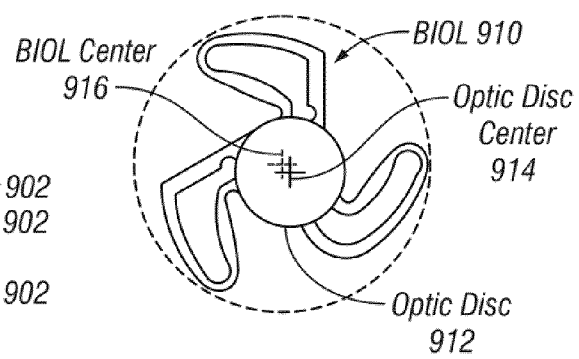
FIG. 9A
FIG. 9B
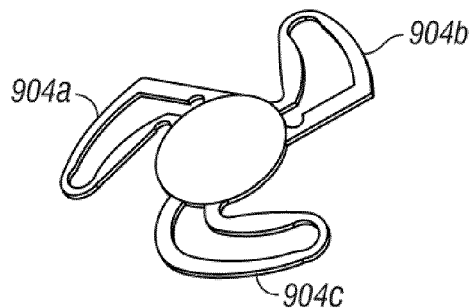
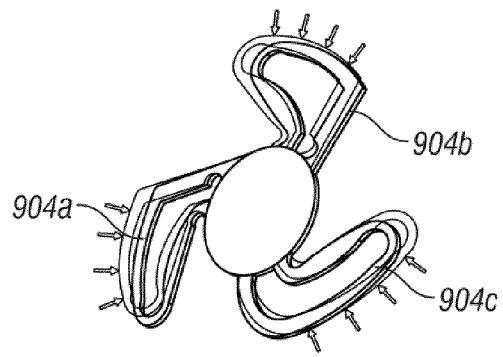
FIG. 9C
FIG. 9D

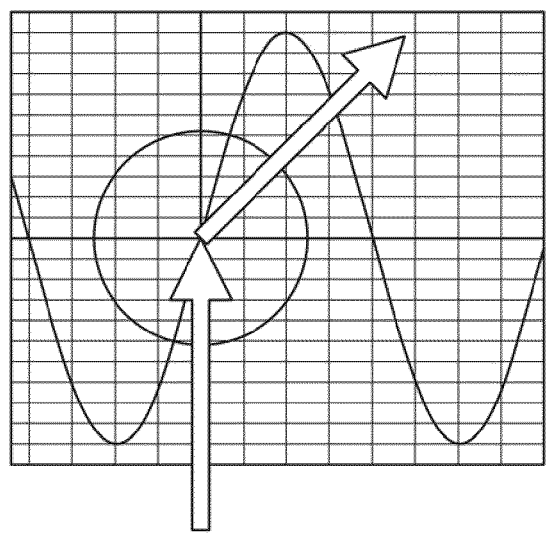
FIG. 12A
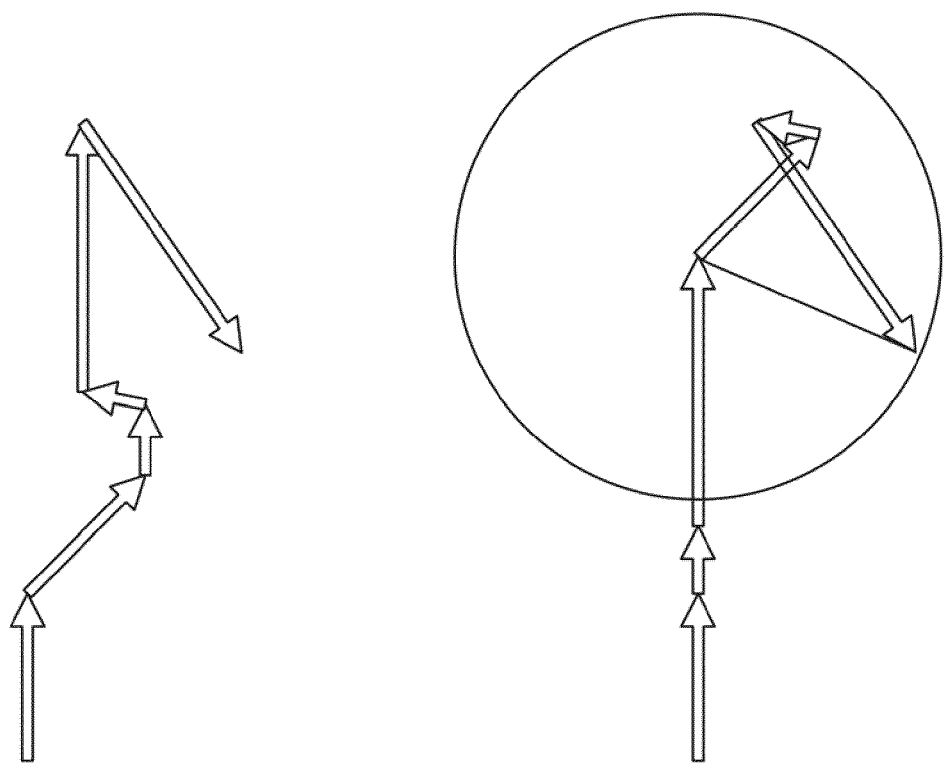
FIG. 12B  FIG. 12C

SYSTEMS AND METHODS FOR IMPLANTING AND EXAMINING INTRAOCULAR LENS

PRIORITY INFORMATION

This application is a continuation of U.S. patent application Ser. No. 12/569,849 filed Sep. 29, 2009, now U.S. Pat. No. 7,878,655 which claims priority from U.S. Provisional Patent Application No. 61/194,721 filed on Sep. 29, 2008, the full disclosures of which are incorporated by reference.

FIELD OF THE INVENTION

This invention relates to systems and methods for replacing a human eye natural lens with a customized biometric intraocular lens.

SUMMARY

Embodiments of the present invention relate to methods, devices and management systems for replacement of a human eye natural lens with a customized Biometric IntraOcular Lens (BIOLs). A system in accordance with one embodiment receives and generates information for automatically manufacturing custom BIOLs that correct both low and high-order aberrations of an eye. The system can also base the design of the BIOL to take into account specific diagnostic conditions, such as environment illumination, subject distance and target results requested by a health care professional or patient.

In accordance with one embodiment, a pre-operative diagnostic device can acquire a patient's biometric data for later constructing a functional model of the patient's eye. Exemplary pre-operative diagnostic devices include an anterior segment analyzer (ASA) and a Lens Prescription System (LPS).

An ASA can acquire a patient's biometric data by imaging sectional images (e.g., meridians) of the anterior part of the patient's eye. Information about cornea and crystalline lens profiles can be generated from these images as well as fixation and pupil position. Based upon this information, a geometric model of the examined eye can be constructed. This geometric model can then be used to generate various types of biometric information, including:

Anterior Chamber Biometry. The anterior chamber biometry can include information relating to different viewing conditions such as far/near and for scotopic/photopic, distances (white-to-white, limbus-to-limbus, anterior chamber depth, axial length, etc.) and anterior chamber (AC) volumes computed from the generated eye model.

Corneal Keratometry. Corneal keratometry information can be a subset of curvature information coming from the front corneal surface that is directly comparable with conventional Keratometry data. Anterior/posterior corneal topographic maps can also be included, such as topographic, instant power, axial power, height values etc. of the computed lens/surfaces.

Corneal Pachimetry Map. The Corneal pachimetry map can be a differential map coming from front/back topographic height maps.

Anterior/Posterior Crystalline Lens Topography Map. The anterior/posterior crystalline lens topography map can be similar to a corneal topography but over the crystalline lens surfaces.

Accommodation Profile. The accommodation profile can dynamically report, in different conditions such as far/near and/or scotopic/photopic, crystalline lens profiles while the examined eye is accommodating.

Pupillometry Profile. The pupillometry profile can be similar to a pupil adjustment.

The ASA can also optionally include an axial length meter configured to measure one or more axial lengths of a patient's eye. In one embodiment, the axial length meter is a plugin-type of module that can be functionally attached to a main body of the the ASA.

In accordance with one embodiment, a wavefront analysis and accommodation analysis performed through an examined eye's visual axis can be used to generate information related to a refractive error of the examined eye, as well as and to a fixation and pupil position. In accordance with various embodiments, the information can include:

Aberrometry Maps. Aberrometry maps can be color-coded maps that report in wavefront modifications caused by the examined eye's optical path.

Accommodation Profile. The accommodation profile can dynamically report, in different conditions such as far/near and/or scotopic/photopic, crystalline lens profiles while the examined eye is accommodating.

Pupillometry Profile. The pupillometry profile can be similar to a pupil adjustment.

Fixation Stability Profile. The fixation stability profile can be similar to a fixation stability recorded while acquiring a video stream.

BIOL and contact lens simulated implant/fitting.

As discussed above, the pre-operative diagnostic device can also include an LPS. An LPS can retrieve patient ocular parameters by collecting various wavefront maps at different depths into the eye and by evaluating distances and positions of the each eye tissue surface. This can be accomplished by use of a layer-oriented wavefront aberrometer and an axial length meter. Data obtained by the LPS can be used construct a functional model of the examined eye and generate various biometric information, including the following:

Biometry of the eye—under different conditions such as far/near and/or scotopic/photopic, information includes distances (white to white, limbus to limbus, anterior chamber depth, axial length, etc.) and AC volumes computed from a generated eye model.

Integral Aberrometric Map—under various conditions described above, provides a wavefront map of the examined eye reporting information on the overall refractive errors of the eye.

Differential Aberrometric Map—under various conditions described above, provides distinct wavefront-maps produced by definite tissue layers placed into the eye and allow us to separate the contribution of the refractive error due to a single layer (cornea or lens) from the others.

Pupillometry Profile—same for the pupil adjustment.

Fixation Stability Profile—same for the fixation stability that is recorded while acquiring a video stream.

In addition, based at least in part on diagnostic examination conditions (such as environmental illumination and subject distance) with respect to an effective visual axis, information pertaining various layers of the examined eye's optical system can be generated, which can provide accurate geometric data for a proper BIOL placement into the eye's capsular bag. A diagnostic device, while aligned to an effective visual axis, can also acquire information about aberrometry of the examined eye's optical system, which can provide accurate functional data of a geometric model within the same or similar environmental conditions.

Embodiments of the present invention can generate accurate designs of BIOLs that fit within the capsular bag of an eye. The physical BIOL design can be obtained using two computational models of the examined eye. A first computational model can be a geometric model that provides a final displacement of the BIOL optics into an aphakik capsular bag. A second computational model can be a functional model that describes an examined eye in terms of aberrations and can also provide a solution for replacement of the natural crystalline lens. The second computational model can also provide a perfect or near-perfect optical design for the optical plate of the lens based, at least in part on, functional refractive behavior of the eye, thereby meeting the patient's expected results at predetermined environmental conditions.

One embodiment of the present invention utilizes a thick-lens calculation process that uses a finite element model (e.g., by using triangular elements) and a back/front ray tracing approach that iterates the calculation until requested parameters are met. In another embodiment, a different algorithm known in the art can be used to generate an optimum lens design.

Furthermore, one embodiment of the present invention provides a solution for implantation of a BIOL, including a proper correct positioning of the BIOL within the patient's eye.

In one embodiment, a diagnostic device coaxially installed into a surgical microscope allows for a determination of a proper location of the BIOL during surgery. The diagnostic device can be a real time intra-operative topographer/aberrometer. Proper use of this device while implanting a BIOL can reduce or eliminate the possibility of misplacements and, thus, consequent refractive aberrations that may prevent the implanted BIOL from working properly.

BRIEF DESCRIPTION OF THE DRAWINGS

FIGS. 9A-9D illustrate features of BIOLs in accordance with various embodiments of the invention.

FIGS. 12A-12C illustrate an amount of light that reaches a detector calculated using vectors.

DETAILED DESCRIPTION OF EMBODIMENTS OF THE INVENTION

In the following description of preferred embodiments, reference is made to the accompanying drawings which form a part hereof, and in which it is shown by way of illustration specific embodiments in which the invention may be practiced. It is to be understood that other embodiments may be utilized and structural changes may be made without departing from the scope of the preferred embodiments of the present invention.

Figure 1:
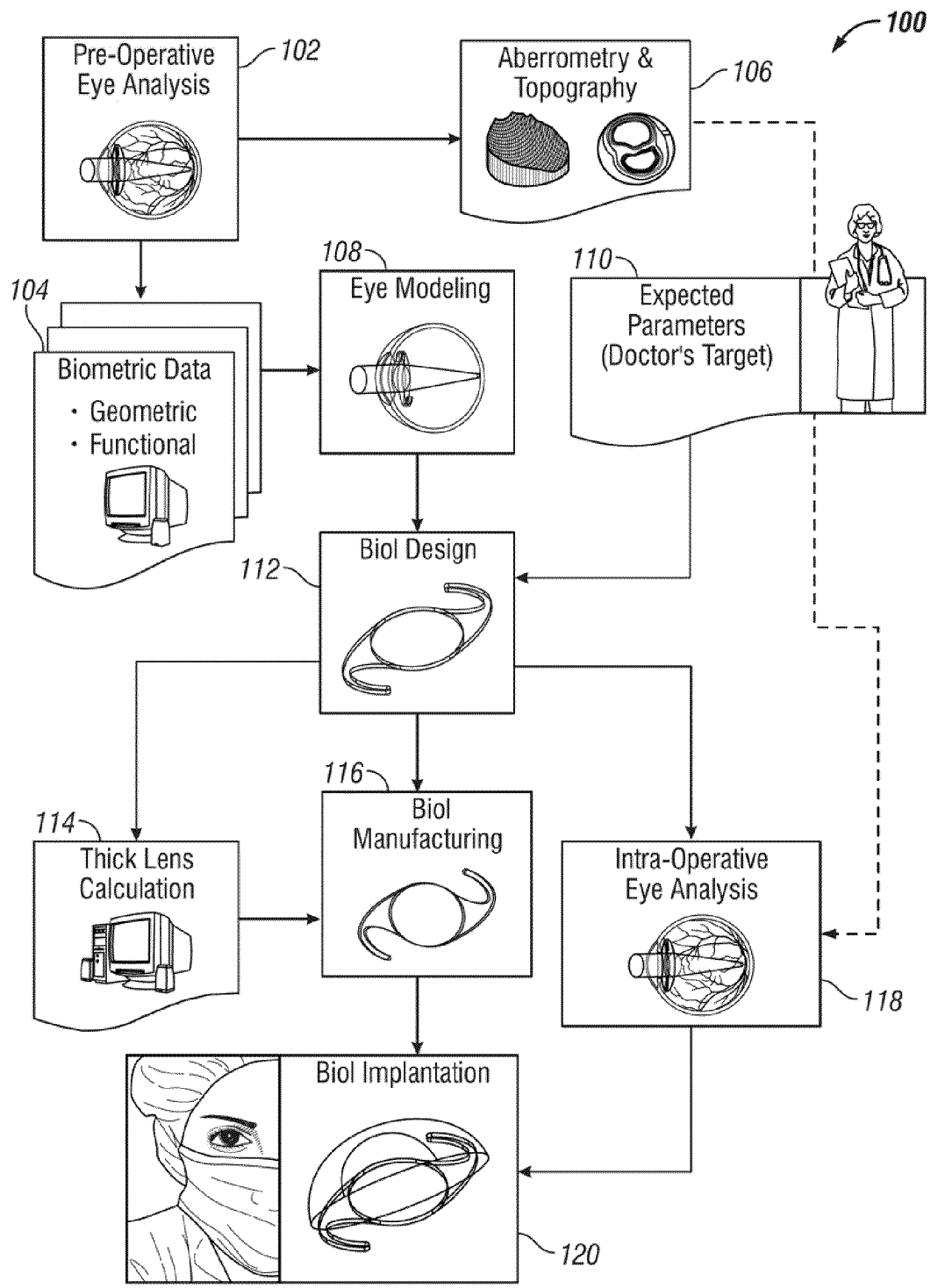
FIG. 1 is a flowchart of a biometric intra-ocular lens (BIOL) design and implantation process according to one embodiment of the invention.

FIG. 1 is a flowchart illustrating an exemplary process 100 for implanting a BIOL in accordance with one embodiment of the present invention. At step 102, a pre-operative eye analysis device, such as the ASA or LPS, analyzes an examined eye to generate data relating to geometrical features and biometric parameters used to design a BIOL for the eye. This can include measurements of the examined eye's functional efficiency in typical environmental conditions. The data is stored in a computer memory at step 104 for later processing.

At step 106, topographic and/or abberometric maps are generated using data obtained during step 102. The topographic and/or aberroetric maps can include colors encoded to represent curvature powers or, in the case of aberrometry, in polynomial wavefronts. A computational model of the examined eye, both geometric and functional, is generated at step 108. Next, at step 110, a surgeon or other healthcare professional, in accordance with the patient, provides parameters for the expected lens functionality (e.g., desired focal distance, Scotopic or Photopic environment, destination use such as for reading, driving or watching TV) in the post-operative eye. A BIOL geometric model that fits the geometry of the previously created model eye (step 108) is calculated at step 112. The BIOL geometric model takes into account decentration and capsular bag dimensions.

The optical surfaces of lens that contribute to the optical efficiency of the patient's eye are then calculated using, for example, a thick lens algorithm at step 114. Stereolithography (STL) computer-aided design (CAD) files are then generated based on the geometric and functional data and the calculated optimized optical surfaces of the lens and sent to a manufacturing system for BIOL production through milling, molding or other production technology at step 116. In accordance with one embodiment, the information sent to the manufacturing system is encrypted prior to being sent for safety and privacy considerations. The information can be sent via a variety of communication methods, including over the Internet or stored on a computer-readable medium and transported to the manufacturing system.

The BIOL is inserted into the patient's eye at steps 118 and 120. To this end, an intra-operative real time analyzer (e.g., RTT) is used to provide position and fixation information for inserting the lens in its proper location and with its proper orientation at step 118. Implantation of the lens is completed at step 120.

Figure 2:
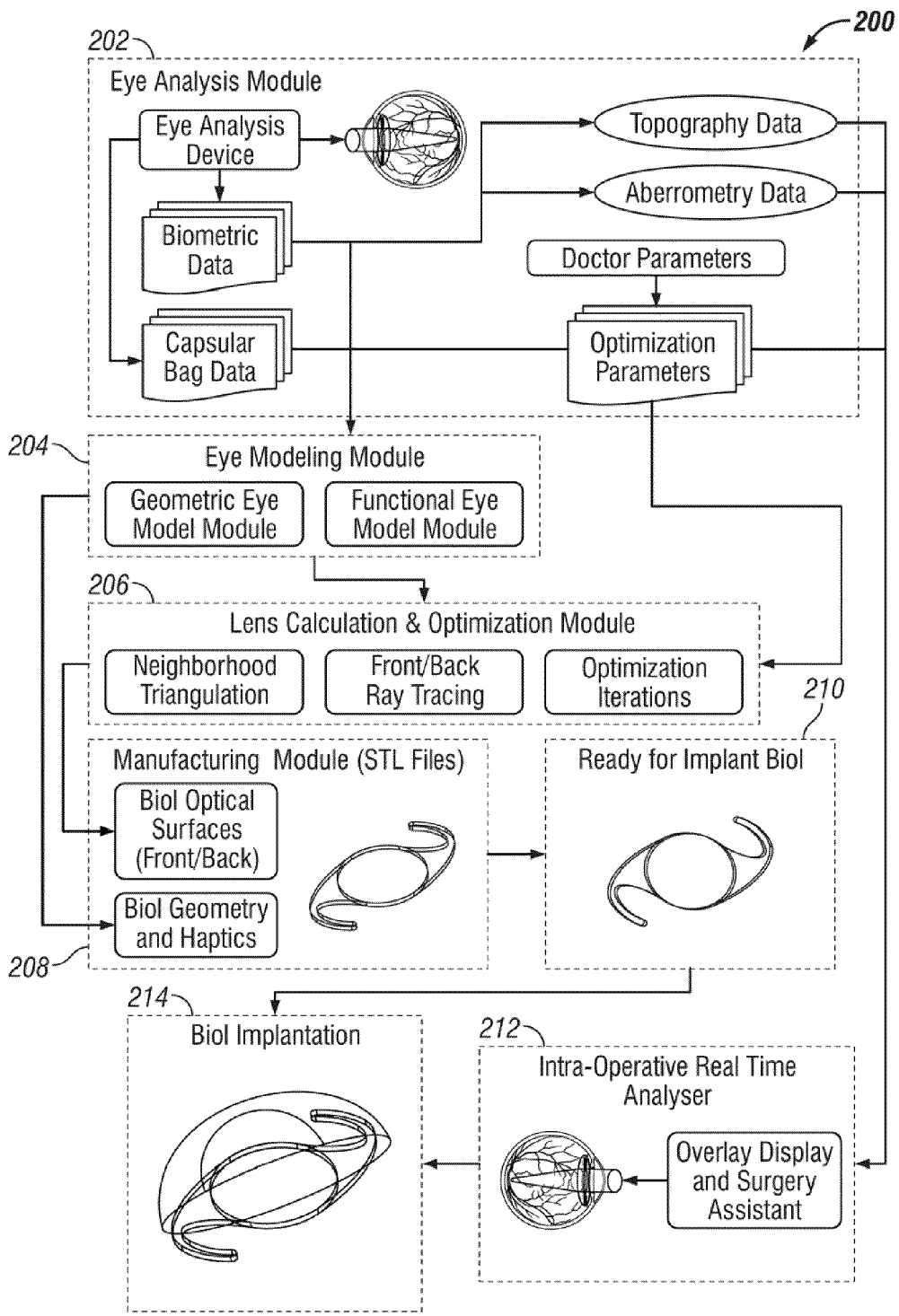
FIG. 2 is a schematic diagram of a BIOL design and implantation system according to one embodiment of the invention.

FIG. 2 is an exemplary schematic diagram of system 200 for designing and implanting a BIOL in accordance with one embodiment of the present invention. The system 200 comprises an eye analysis module 202, an eye modeling module 204, a lens calculation and optimizing module 206, a manufacturing module 208 and an intra-operative real time analyzer module 212.

The eye analysis module 202 is operable to provide biometric and functional information (e.g., curvature profiles, topographies, pachimetry, aberrometry, pupillometry, accommodation profiles, anterior chamber depth, axial length, etc.). The eye analysis module 200 can also be used to receive additional input parameters from a healthcare professional (e.g., doctor). The parameters can include a desired focal distance, whether the patient will typically be in a scotopic or photopic environment, and what the patient will typically be using the BIOL for, such as reading, driving or TV viewing. In accordance with one embodiment, a single device may incorporate the functionality of the eye analysis module 202.

The eye modeling module 204 calculates a final lens design for manufacturing. In accordance with one embodiment, the eye modeling module 204 receives raw data from the eye analysis module 202 and generates two distinct computational models: a geometric eye model and a functional eye model. The geometric eye model describes a geometry of an anterior part of the eye being examined. The functional eye model describes functionality of the eye.

Lens module 206 calculates and optimizes optical surfaces of the BIOL to fit a health care professional's expected parameters. These parameters were inputted into the eye analysis module 202, as described above. In one embodiment, the lens module 206 uses a thick-lens algorithm to optimize the optical surfaces o the BIOL.

The manufacturing module 208 generates STL files based on information received from the eye modeling module 204 and the thick lens calculation and optimization module 206. The STL files describe specifications of the BIOL for producing a final BIOL 210 using a 3-dimensional manufacturing system.

The real time intra-operative analyzer 212 is used to implant the BIOL 210 in an appropriate position and with a proper orientation in the patient's eye 214. In one embodiment, the real time intra-operative analyzer is an RTT, which is discussed in more detail later.

Figure 3:
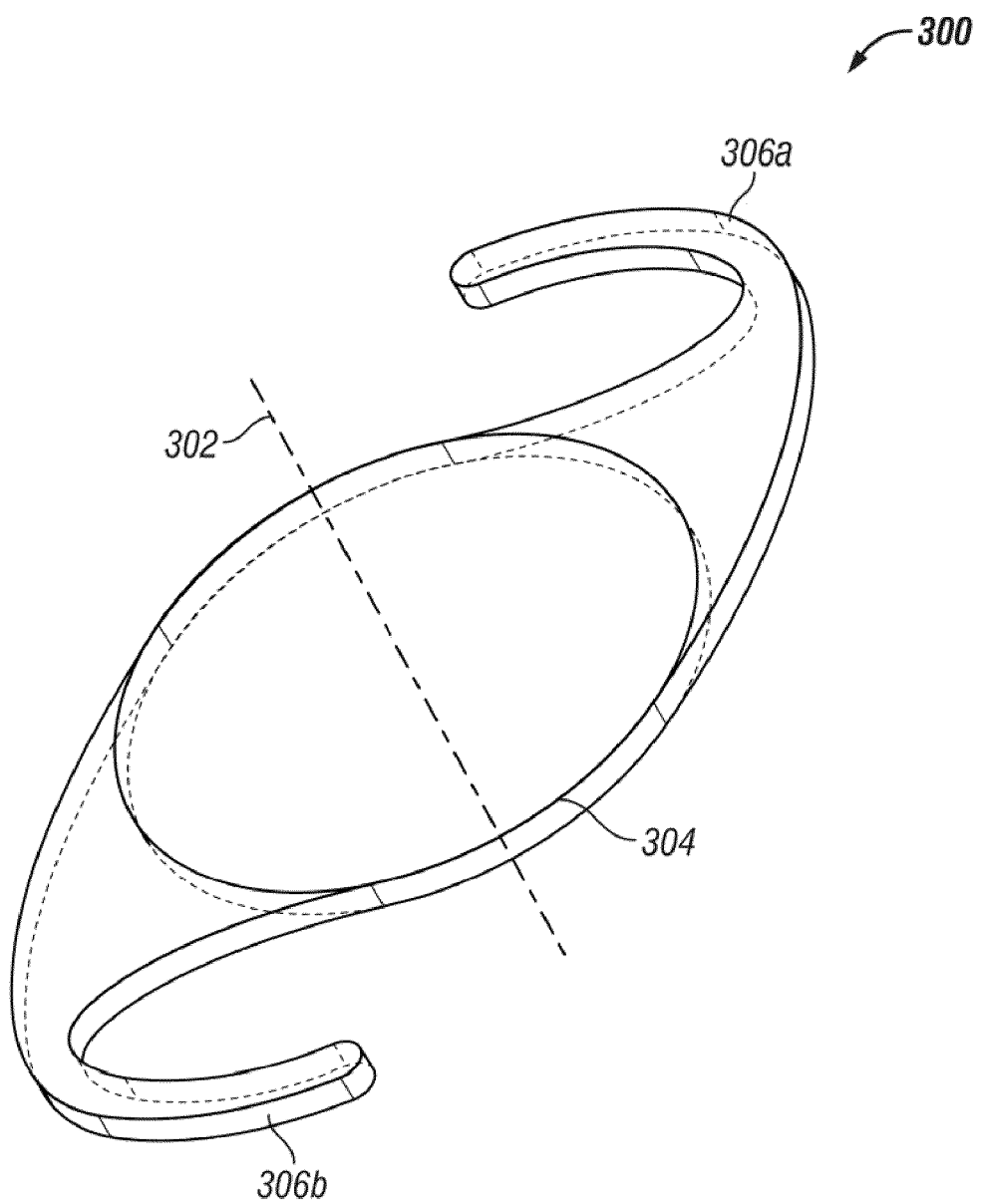
FIG. 3 is a perspective view of a BIOL according to one embodiment of the invention.

FIG. 3 is a perspective view of an exemplary BIOL 300 in accordance with one embodiment. FIG. 3 illustrates an optical axis 302 that does not extend through a geometrical center of the BIOL 300, but instead overlaps a patient's visual axis of pertaining to the eye in which the BIOL is to be implanted. The BIOL 300 includes an optic disc 304 and parametric haptics 306a and 306b extending from the outer circumference of the optic disc. The optic disc 304 can be customized to a particular patient for correcting high-order aberrations. The parametric haptics 306a and 306b can be designed to position the optic disc in a pre-calculated position within a patient's eye. In the embodiment of FIG. 3, the BIOL includes two haptics, but in other embodiments, a different number of haptics can be used, including no haptics, one haptic, three haptics, four haptics, etc.

Figure 4:
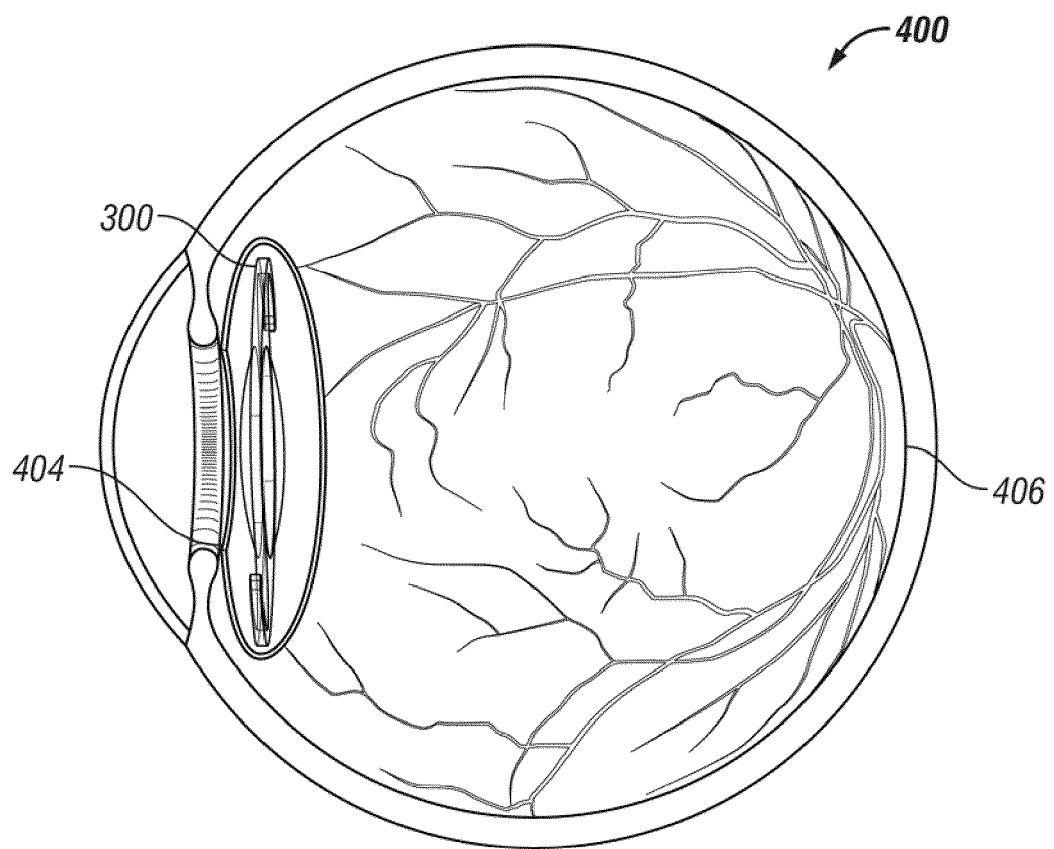
FIG. 4 is a cross-sectional view of a human eye with a BIOL implanted therein according to one embodiment of the invention.

FIG. 4 is a cross-section of an eye 400 with BIOL 300 implanted therein. FIG. 4 illustrates the BIOL 300 positioned inside a capsular bag 402 of the eye, with the optical disc 302 of the BIOL 300 aligned with the iris aperture of the eye 404 so that light entering through the iris aperture 404 is properly focused at a focal point 406 on the eye's retina.

Figure 5:
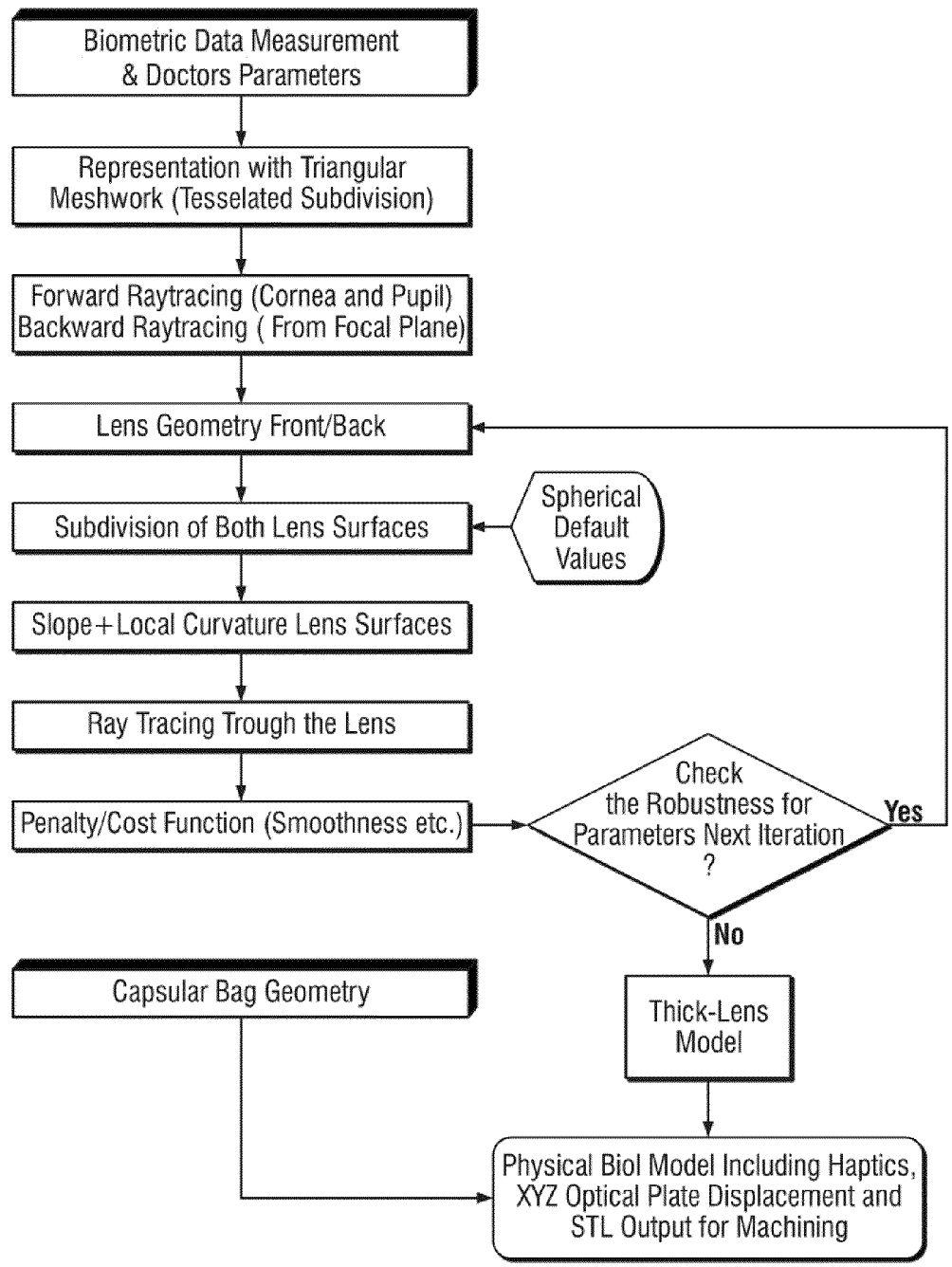
FIG. 5 is flowchart of a thick-lens calculation process according to one embodiment of the invention.

FIG. 5 is a flowchart illustrating a thick-lens calculation process 500 in accordance with one embodiment. The thick-lens calculation process 500 can be performed using thick-lens calculation and optimization module 206 of FIG. 2.

A thick-lens optical model can be defined by a BIOL surface calculation using a boundary finite element model, with tessellated triangular elements (FIG. 9A).

Figure 7A:
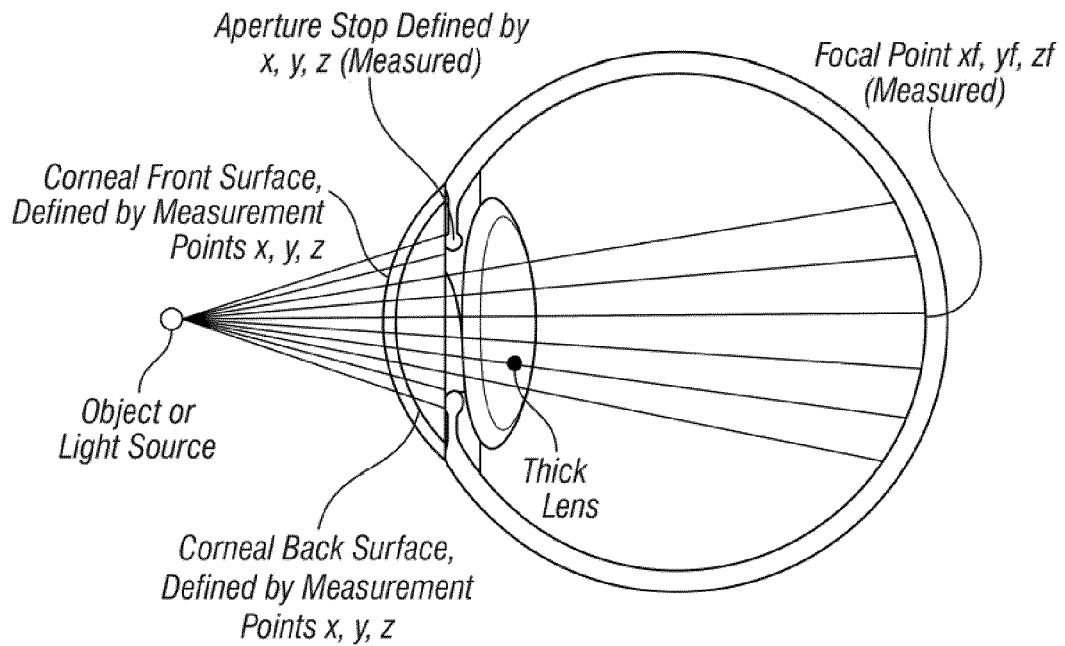
FIGS. 7A and 7B are illustrations of front ray tracing using non-collimated and collimated rays, respectively, according to one embodiment of the invention.
Figure 7B:
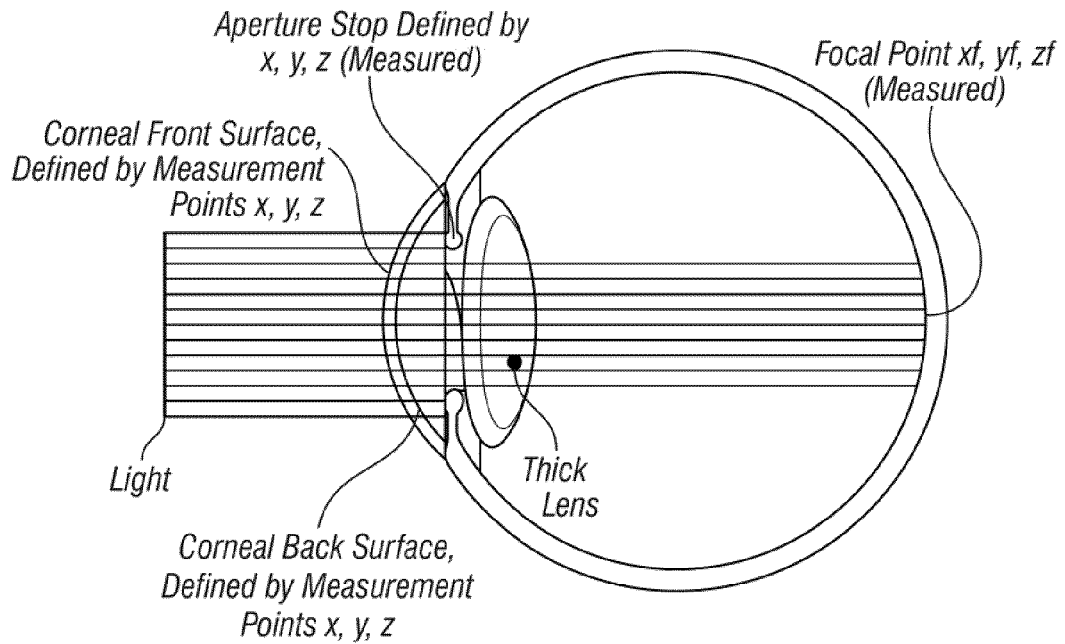

In accordance with one embodiment, a best fit intraocular lens implant can compensate for some or all aberrations of an examined eye cornea by transforming an incident bundle of rays into a smallest possible focal point located at the retinal plane of the examined eye (FIGS. 7A and 7B). A non incident bundle of collimated rays (FIG. 7A) or a flat spherical wavefront (FIG. 7B) is projected into the examined eye aperture. A subdivision schema based on triangulation is used to describe both front and back surfaces of the thick lens, where each triangle normal contributes to a definition of the slope. All triangles in a neighborhood can also define an overall curvature.

Forward ray tracing is projected from an object or light source through the aperture toward the retinal focal point. Also a backward ray tracing generated from the focal point toward the eye aperture stop, characterized by equi-angular spaced rays, provided a homogeneous intensity profile adjacent to the focal point $zf \pm \Delta$.

This approach may not have a unique solution for the rays/surface intersection, so dintersections that give a smooth (at least $C^{(1)}$ or $C^{(2)}$) and convex (globally convex) surface may be found. The iteration may continue until the smallest Airy disk is reached. The algorithm can optionally weight a solution for robustness (least sensitivity), optimizing the surface curvature for the following parameters: decentration of the lens; axial displacement of the lens; lens tilt and rotation around the z-axis; geometry of the aperture stop; and object distance (e.g., favorite scope of the lens).

Figure 8A:
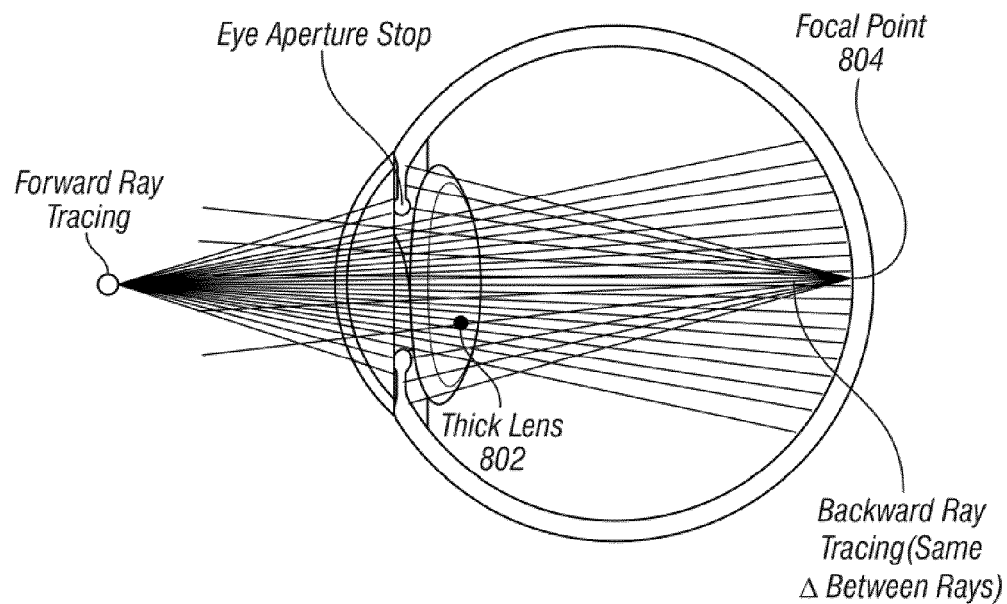
FIG. 8A is an illustration of front and back ray tracing of an eye, according to one embodiment of the invention.
Figure 8B:
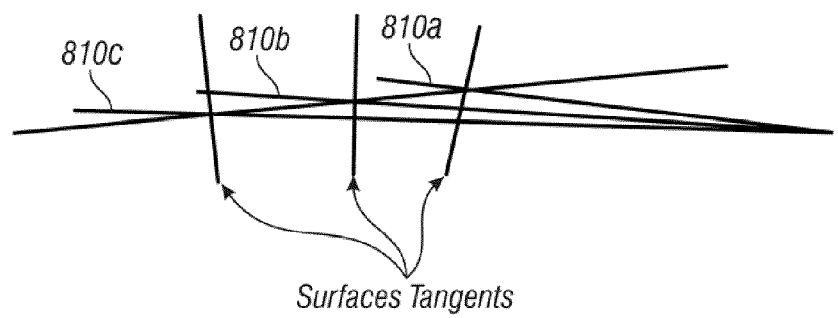
FIG. 8B illustrates equi-angular rays emanating from a focal point according to one embodiment of the invention.

FIGS. 7A and 7B illustrate alternate techniques to for forward ray tracing in accordance with one embodiment. FIG. 7A illustrates forward ray tracing with non-collimated rays and FIG. 7B illustrates forward ray tracing with collimated rays FIG. 8A illustrates forward and backward ray tracing of the thick lens 802 in accordance with one embodiment. The forward ray tracing uses non-collimated rays and the backward ray tracing uses equi-angular spaced rays coming from the retinal focal point 804. FIG. 8B illustrates equi-angular spaced rays 810a, 810b, 810c.

FIGS. 9A-9D illustrate BIOLs in accordance with various embodiments. FIG. 9A is a perspective view of BIOL 900 having a section of the BIOL 900 magnified to illustrate tessellated triangular elements 902. Tessellated triangular elements 902 can be used during modeling the BIOL 900 to assist in defining the slope or overall curvature of the optical disc section of the BIOL 900. In accordance with one embodiment, the outer surface of the lens is smooth, however; not defined by the tessellated triangular elements. In other words, in one embodiment, the tessellated triangular elements are used only during modeling of the BIOL.

In accordance with one embodiment, the design of the BIOL 900 is based on data provided by the eye analysis module 202 to parametrically dimension the lens parts. This allows proper positioning of the optical center of the optical plate of the BIOL on a best center (reported by the pupillometry exam of the ASA, for example) of the patient's eye visual axis.

FIG. 9B illustrates an exemplary parametric BIOL 910 that has optical disc 912 decentered from the geometrical center of the BIOL construction axis. As illustrated, a the center of the optic disc (identified by hash mark 914) is different from the geometrical center of the BIOL (identified by hash mark 916). The decentration amount can be based on information obtained during a pupillometry exam selected behavior of the BIOL. Planning a result of BIOL implant can be based on possible prediction of presbyopic symptoms. Thus, a practical solution for a BIOL implant could range from near to intermediate to distance focal points that are shifted spatially in terms of a center of visual axis.

In accordance with one embodiment, a pupillometry exam reports different pupil centers in different conditions, thereby helping patients with astigmatism to consider choosing presbyopia-correcting BIOL and to be aware of an amount of glare and halo they may expect to experience.

Capsular bag geometrical information can also be used to parametrically design, driven by an automatic CAD process, dimensions for construction of the haptics (e.g., length, loops, thickness, number, shape, etc.) and optical disc displacement so, after implantation, the optical disc is accurately placed with respect to desired visual axis.

An iterative process using a finite element method (FEM) analysis can be used to compute forces and shifts that occur when the BIOL is implanted into the capsular bag of the patient's eye. In accordance with one embodiment, a library of different haptics designs that are suitable for different situations can be used to provide an optimal haptic for specific situations.

As illustrated in FIGS. 9C and 9D, both first haptic 904a and second haptic 904b have smoother designs to bear greater forces and a smaller angle of bend as well as clearance. In contrast, a third haptic 904c has a sharper and more elongated design to give a lower peripheral push force resistance, allowing a larger angle of bend and motion clearance.

The BIOL optical disc may slightly rotate, tilt or dislocate after implantation. When the lens is constructed to correct astigmatisms or high order aberrations, the proper orientation of the optical disc may be particularly important. The rotation, tilting and dislocating effects can be minimized or avoided by accurately predicting the capsular bag dimensions and shrink as well as how much residual accommodation is expected. To this end, accommodation data can be used to predict how much of the residual ciliary body work is expected in the follow up period after implantation. This may be related to a final displacement of the posterior face of the BIOL that should firmly push backward into the posterior capsule surface (causing a perfect adherence between the posterior capsule and the posterior surface of the BIOL). This force can be calculated to compensate for common ciliary body work but also to be strong enough to stretch the capsular bag to place the back surface of the lens in the proper focal plane (e.g., the natural lens back surface both in accommodated and relaxed status). When the lens design is generated, a stress analysis can be conducted to verify strength of the components and a simulated life cycle can be simulated to prevent or reduce the possibility of lens dislocation events.

As discussed above, various devices can be used to analyze a patient's eye for the purposes of obtaining data to generate the BIOLs and provide data for proper implantation of the BIOL in the patient's eye. Exemplary devices that can be used for such purposes will now be discussed in more detail below.

Anterior Segment Analyzer Device (ASA)

The ASA pre-operative diagnostic analyzer can comprise a dual-Scheimpflug camera system that captures several images and extracts meridian profiles (FIGS. 6A and 6B) of the anterior part of an eye. The preoperative diagnostic device can then reconstruct a three-dimensional geometric model of the examined eye and generate an accurate aberrometry of the eye, properly aligned on a current visual axis, putting the aberrometric (functional) data in true relation with a geometric model. The ASA is based on an implementation of a dual-Scheimpflug camera that captures images and extracts meridian profiles of the anterior part of an eye. Based on the extracted information, the ASA is then able to construct a three-dimensional geometric model of the examined eye. The ASA is also capable of producing an accurate aberrometry map of an eye, properly aligned on the current visual axis, putting the aberrometric (functional) data in true relation with the geometric model. The ASA device is described in more detail in PCT Patent Application No. PCT/IB2008/003956, filed on Dec. 19, 2008 and entitled "Dual Scheimpflug System For Three-Dimensional Analysis of an Eye," the full disclosure of which is incorporated by reference.

In accordance with one embodiment, the ASA can also include an axial length meter to measure one or more lengths of a patient's eye. Such an axial length meter can be similar to the axial length meter used in the LPS, discussed in more detail below.

Figure 6A:
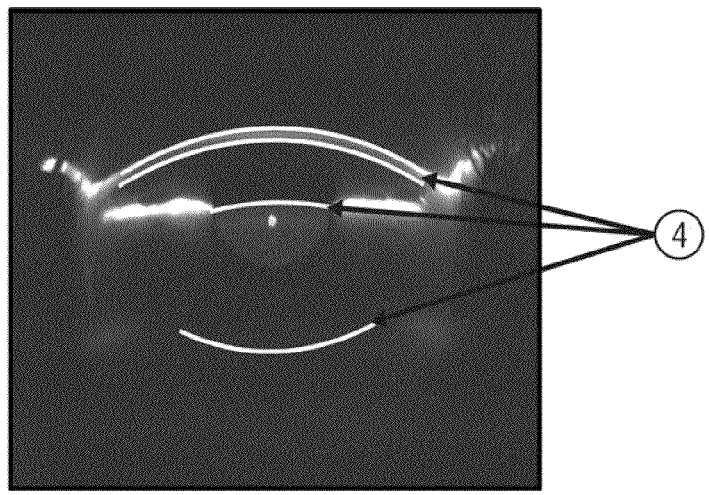
FIGS. 6A, 6B and 6C are an image of an eye taken by a first Scheimpflug camera, an image of a pupil taken by a pupil camera, and an image of an eye taken by a second Scheimpflug camera, respectively, according to one embodiment of the invention.
Figure 6B:
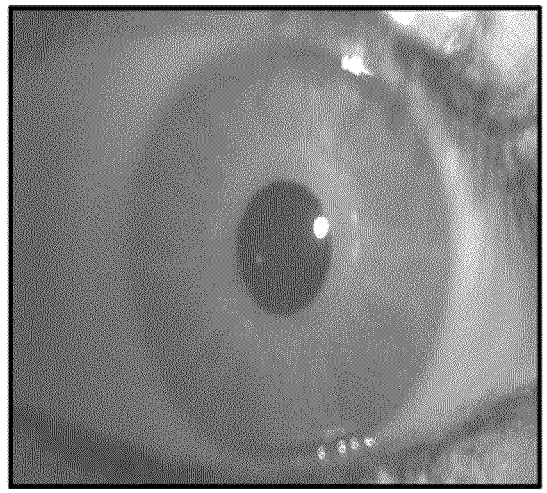
Figure 6C:
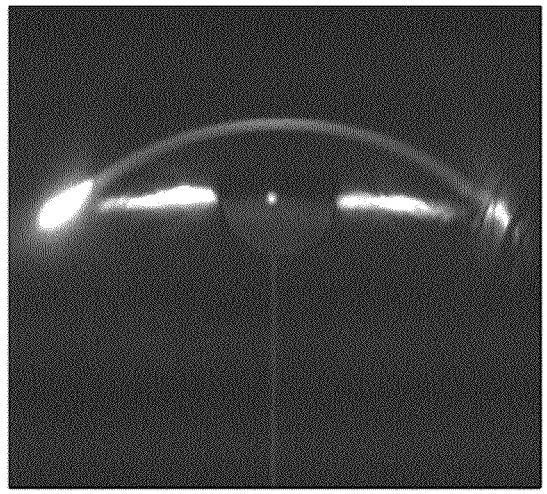

FIGS. 6A, 6B and 6C are images of an eye using first and second Scheimpflug cameras and a pupil camera in accordance with one embodiment. To this end, FIG. 6A illustrates a profile image of an eye using a first Scheimpflug camera, FIG. 6B is an image of an eye using a pupil camera, and FIG. 6C is a profile image of an eye using a second Scheimpflug camera. The images of FIGS. 6A, 6B, 6C can be captured by the pre-operative analyzer 202 of FIG. 2, for example. The pre-operative analyzer may also be used to enhance the profile images generated by the first and second Scheimpflug cameras, as described in more detail above with regards to the thick-lens calculation process 500.

Lens Prescription System (LPS)

The LPS can be used to measure parameters of the anterior chamber of an eye for use in generating or selecting a proper BIOL for a specific patient. One embodiment of the LPS can be generally described as a layer oriented wavefront sensor analyzer that generates data used to create maps representing topographic layers of the inner volume of the eye (thus giving information on corneal and lens tissues) as well as the out coming wavefront by projecting semi-coherent light sources on the retina.

In accordance with one embodiment, the LPS can include an optical head mountable on a mechanical system that allows automatic alignment with the eye of the patient. The LPS can also include a fixation target system, capable of compensating the examined eye refractive error, to help the patient to look in the correct direction.

The LPS can also include a differential aberrometer and an axial length meter working together, to measure a complete set of information suitable to choose an IOL, design a custom IOL or identify where refractive error causes are located. The aberrometer can be based on a multi-conjugate wavefront system, which delivers the evaluation of the aberrations of all the optical subsystems of the eye, and on an axial length meter, which measures a distance between different layers of an eye, such as the cornea, lens and retina layers. Knowing a total aberration and the corneal and lens aberrations, a surgeon or other health care professional can identify where the refractive error is located, and plan the surgery based on the data in conjunction with the axial length data.

As discussed above, the LPS can include an axial length meter to measure various axial distances between layers of an eye. Such a device can use the principles of laser Doppler interferometry, which reaches a high level of spatial resolution. In a different embodiment an axial length meter can be assembled based on the time to flight laser rangefinder principle, as shown in the picture below. In another embodiment, an axial length meter can be realized using optical low coherence interferometry. In yet another embodiment, a phase-shift laser rangefinder can be used to the phase shift of waves reflected backwards from the inner surfaces of an eye with respect to the waves running on an inner reference path.

The following describes one embodiment of the LPS. In this embodiment, the LPS includes a wavefront sensor based on a sinusoidal pattern plate designed to be used with layer oriented sensors. A layer oriented technique is used to obtain a topographic representation of an eye to be analyzed. The LPS combines of both concepts to provide volume information on the inner structure of the eye.

Figure 10A:
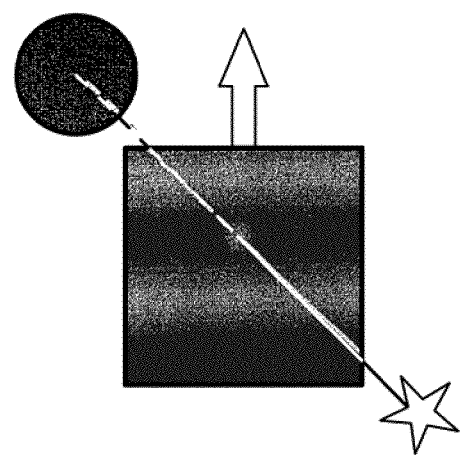
FIGS. 10A-10C illustrate a reference light hitting different locations of a sinusoidal pattern.
Figure 10B:
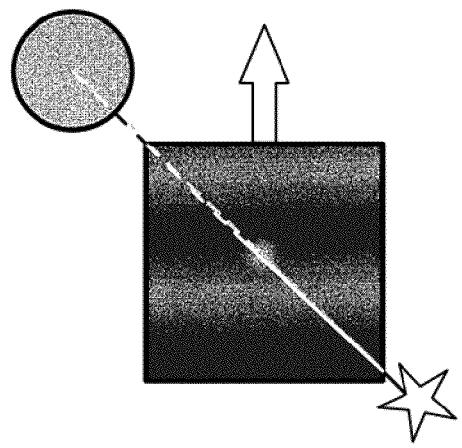
Figure 10C:
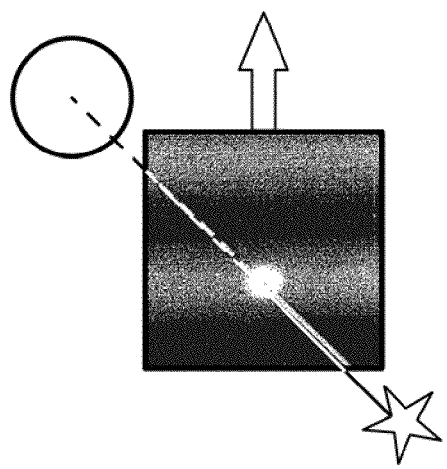

A sinusoidal plate concept is discussed with reference to FIGS. 10A-10C. The sinusoidal pattern plate concept involves placing an optical window with a transmission that varies sinusoidally along one axis between 0% and 100% on the focal plane, and a detector on a subsequent pupil plane, on the way to reconstruct a global and local tilt of a wavefront in one direction. To illustrate, consider the light from a single reference point source, in absence of perturbations. The effect on the image of the pupil (which is uniformly illuminated, because the light from the reference is collimated) in the presence of the sinusoidal pattern is shown in FIGS. 10A-10C. If the light of the reference focuses where the transmission of the pattern is minimum (0%), the pupil will be dark (FIG. 10A), but moving the pattern along the axis (shown by arrows in FIGS. 10A-10C) orthogonal to the sinusoidal modulation, one can see that the luminosity of the pupil varies uniformly as a function of the point of the sinusoid where the image of the reference lies (see FIGS. 10B and 10C). The presence of the sinusoidal pattern allows detection of a signal which is proportional to the movement of the object on the focal plane or, in other words, to its tilt.

To illustrate further, a global tilt on the wavefront can be introduced. The effect is a movement of the reference image on the focal plane, which is proportional to the first derivative of the wavefront itself. So, if the sinusoidal pattern is fixed, the result is the same described for a moving pattern in absence of perturbations. For a given tilt, if the image of the reference forms where the derivative of the transmission of the pattern is maximum (that is to say where the phase of the sinusoid is $\pi/4$ and the transmission is 50%), the detected signal corresponding to the tilt of the reference light source will be maximum as well. Being in the linear part of the sinusoidal pattern, even a small movement of the reference can cause a significant change of the pupil illumination if the period of the sine is chosen in an appropriate way. If the image of the reference forms where the transmission of the plate is maximum or minimum, in both cases, a small movement of the reference in the focal plane due to a tilt will either not be detected or barely detected, being the change of illumination at the pupil level is negligible or very small.

In order to obtain the tilt in both axes, the light coming from the reference can be dived in two parts (e.g. using a beam splitter) and analyzed by the introduction of two orthogonal sinusoidal patterns.

Figure 11A:
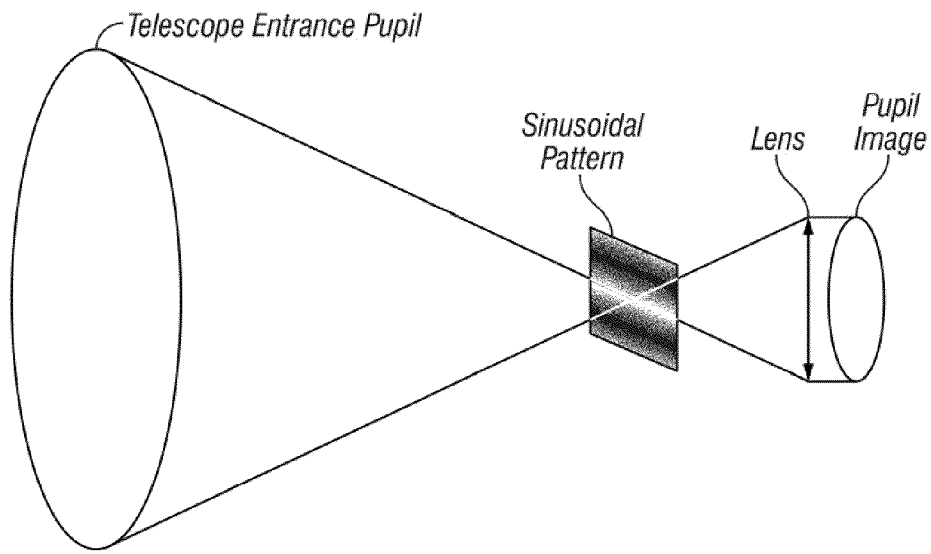
FIGS. 11A and 11B illustrate a comparison between an entire pupil pattern and a portion of a pupil pattern imaged through a sinusoidal pattern.
Figure 11B:
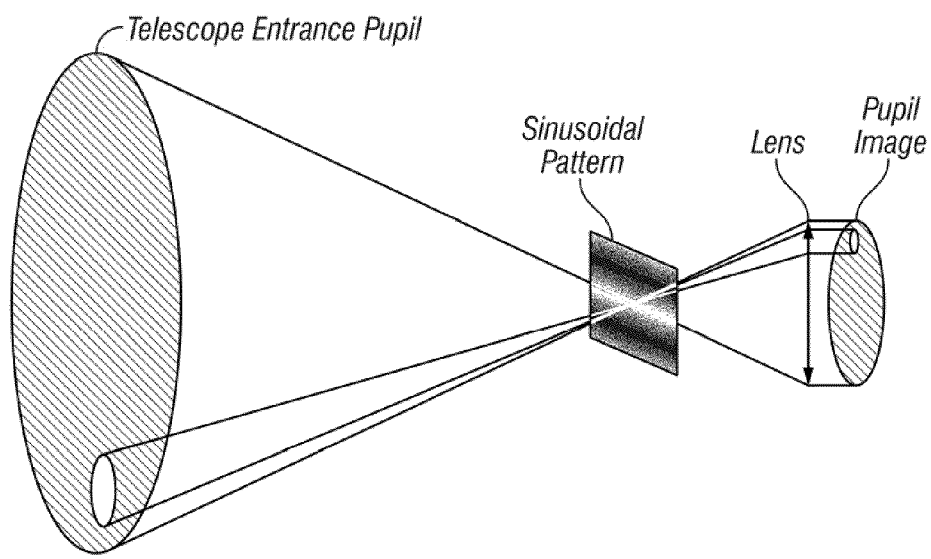

As a detector is placed in a pupil plane (or, in layer-oriented fashion, conjugated at any specific range) one can focus on the light collected from a single sub-aperture to determine tip-tilt. To illustrate, a comparison between the image of an entire pupil plane and part of the pupil plane is shown in FIGS. 11A and 11B, respectively. Here, a mask is placed on an entrance pupil of the system in FIG. 11B. A selected sub-pupil behaves like the pupil in the previous example (FIGS. 10A and 10B), so a time-variable tilt of the wavefront in the sub-pupil produces the same or similar modulation in intensity predicted for the entire pupil. Thus, in order to detect the high-orders of distortion of the wavefront, one can analyze the intensity of the light of the reference on a number of sub-apertures of the entrance pupil of the system.

The signal one can obtain from each sub-pupil is proportional to the first derivative of the wavefront, which is the local tilt on that sub-aperture. Described another way, the wavefront sensor provides a map of the local tip-tilt in each sub-aperture. The sampling of the pupil is determined at the level of the detector, giving allowance for re-binning to adjust the spatial sampling to a desired one.

Such a local, specific of a single sub-aperture, tip-tilt translates into a modulation of light onto the detector placed on the pupil plane. Such a modulation shows up half of the light of the reference in the considered sub-aperture, plus the projection along one fixed axis of a vector whose length is, again, equal to half of the light of the reference, rotated by an amount corresponding to the phase of the sinusoidal pattern where the reference light is falling over. If in one position the reference is just on the point of maximum variation of the transparency with the tip-tilt movement, or close to it, the gain can be enough to detect the local tip-tilt. So, in the case of a single reference, one can place the sinusoidal pattern in order to find the reference in the central position between the minimum and the maximum of transmission, to maximize the output signal. The step of the sinusoidal pattern should be large enough to avoid wrapping around this information, and not so large that the signal becomes too weak. In practice, the RMS of the tip-tilt fluctuation can be in order of one phase radian.

When a large number of references is involved, each of these references contributes to the formation of the pupil image and each is modulated by local tip-tilt in the same fashion. Because of the sinusoidal transparency of the pattern, one can consider that the amount of light from a reference that reaches the detector is the sum of two vectors, the first fixed and the other free of rotation, with the same phase of the pattern in the position where the image of the reference lies. While half of the light of the whole set of references reaches the detector, the other half is piled up, generally speaking, in a random-walk summation way, as illustrated in FIGS. 12A-12C.

The amount of light that reaches the detector can be calculated by using vector calculus. In FIG. 12A, the light of a single reference, lying where the transmission of the pattern is 50%, considered as the sum of two vectors, the module of which is half the intensity of the reference on the focal plane. The direction of the first vector is fixed, while the second rotates with the same phase of the sinusoidal pattern. FIG. 12B shows the sum of the contributions of three references in the field. A representation of the vectors summed in a way to separate the "fixed" component from the "rotational" one is shown in FIG. 12C. A period of the sinusoidal pattern corresponds to a complete rotation of the resultant of the three rotational vectors.

If a large number of references are chosen randomly positioned, some of them will give a good signal, some of them a weak signal and some of them a signal close to zero; depending upon where each reference lies in the focal plane and where the sinusoidal pattern plate is positioned, as explained before and shown in FIGS. 11A and 11B. In FIG. 13A this situation is represented, where a large number of references are considered and the shape of the sinusoidal pattern plate is a regular one; of course, the signal obtained at the pupil level can be maximized by moving the plate left and right (in the case shown in the figure) in order to maximize the number of reference lights falling in a position on the plate which corresponds to a phase of the sinusoid of $\pi/4$ and to a light transmission of ~50%.

Figure 13B:
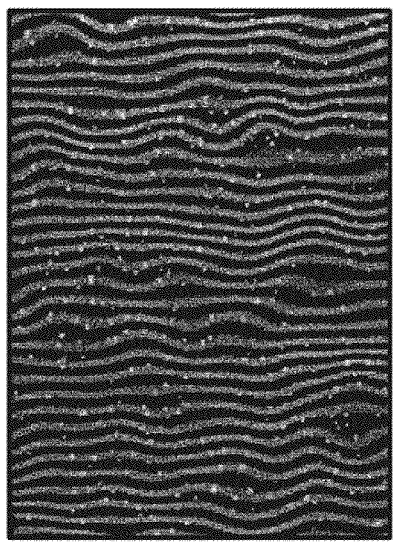
FIGS. 13A-13D illustrate reference fields superimposed on different sinusoidal pattern plates.
Figure 13D:
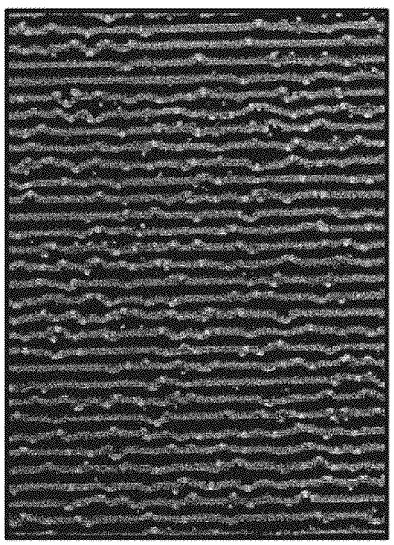
Figure 13A:
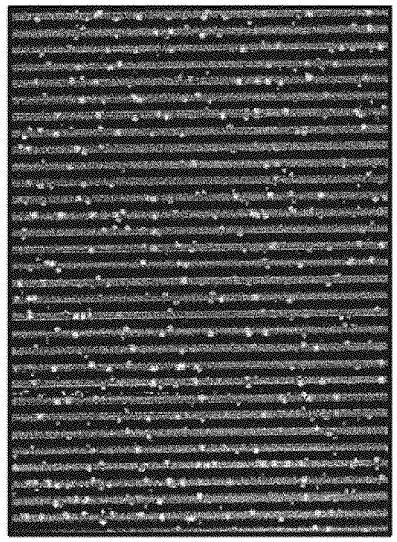
Figure 13C:
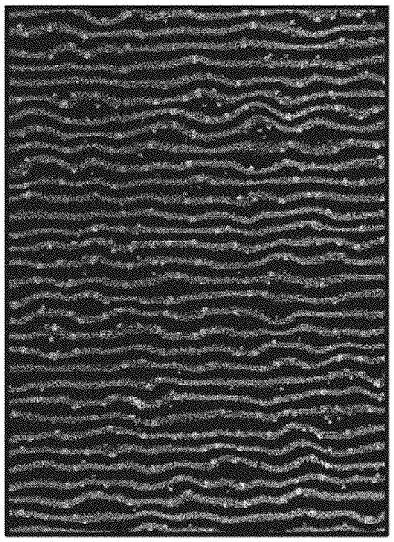

When the references are randomly placed in the field, the plate can be designed as shown in FIGS. 13B-13D, with the aim of maximizing the number of references falling on the plate where the light transmission is about 50%. Of course, precise knowledge of the reference positions, design of custom made plates and careful positioning of the plates can be used as well.

Thus, FIGS. 13A-13D illustrate crowded reference fields superimposed on a sinusoidal pattern plate. In FIG. 13A, the pattern is straight and regular; the signal strength is small and depends slightly on the position of the references inside the pattern. Starting with FIG. 13B and progressing to FIG. 13D, illustrate that an increasing tuning of the distortion makes the signal stronger and stronger, but requires more and more precise alignment with the references.

Figure 14:
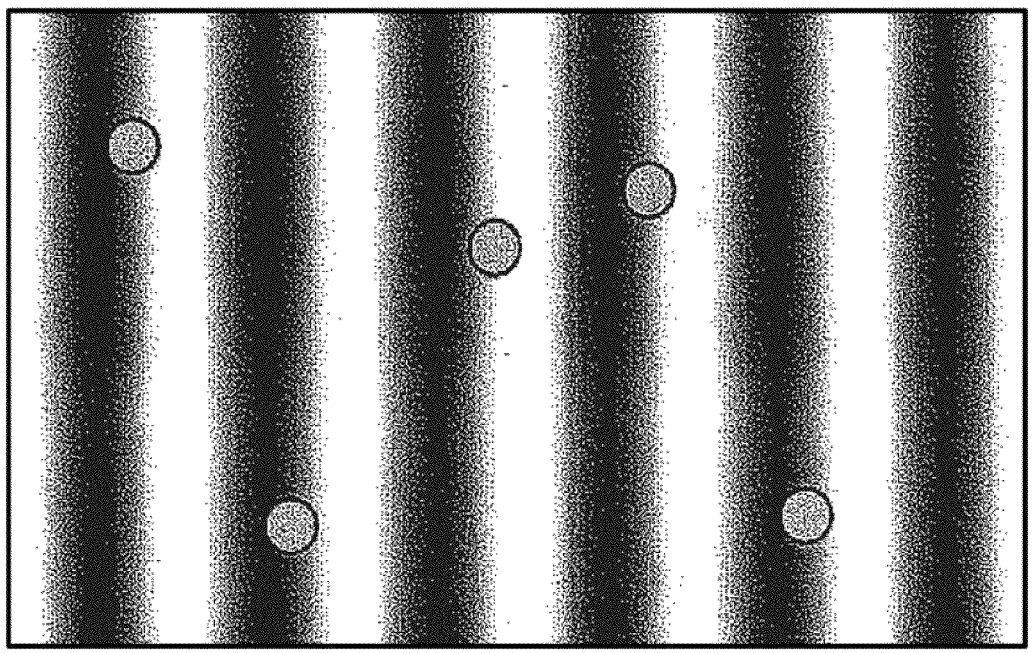
FIG. 14 illustrates a proper positioning of an artificial reference in accordance with one embodiment of the present invention.

FIG. 14 illustrates that a proper positioning of artificial references. The sources are positioned where the sinusoidal pattern transmittance is near 50% and thus giving the maximum over the pattern movement or "wavefront tilting." A 50% transmittance location can be the optimum position for the references.

A layer oriented (LO) technique can be described as having the wavefront sensors looking to a certain number of references simultaneously, superimposing optically the light coming from all the references at the level of the detectors, where an image of the entrance pupil of the system is created. To perform this operation, pupil plane wavefront sensors can be used, such as a pyramid, sinusoidal pattern plate or curved pattern plates.

This means that, instead of having one wavefront sensor (WFS) for each reference, like in conventional Multi Conjugated Adaptive Optics (MCAO) systems, in the LO approach the number of WFSs used in the system is dependent on the number of turbulent layers that are explored at the same time. If a volume is to be scanned and the aberration inside this volume are static, different depths inside this volume can be conjugated by moving a detector plane along the focus movement.

Figure 15:
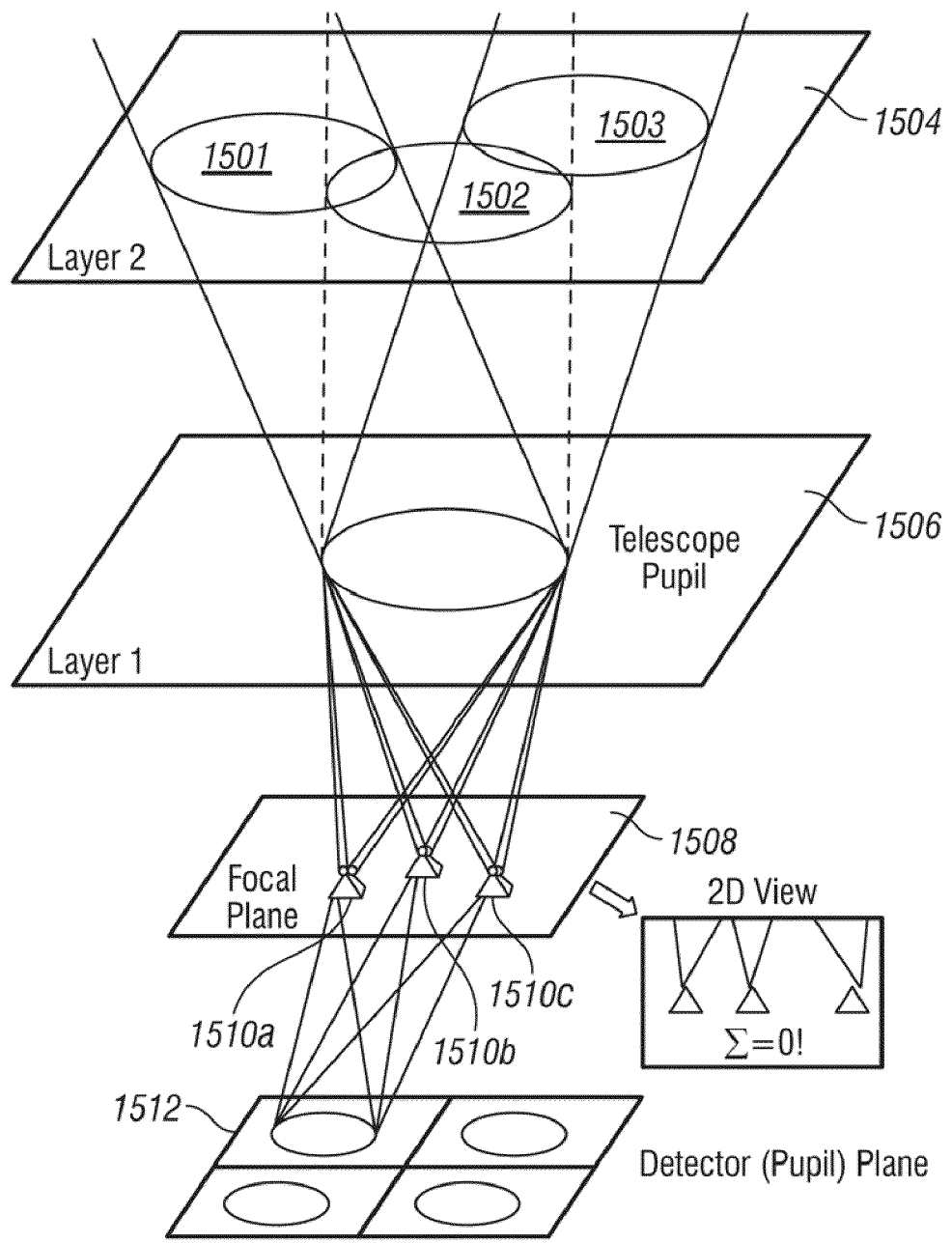
FIG. 15 is a schematic illustrating optical co-addition of light using a layer orientated technique in accordance with one embodiment of the present invention.

In FIG. 15, light received from three references 1501, 1502 and 1503 is superimposed, passing through a volume having layers 1504 and 1506, and collected from an optical system (e.g., a lens—not shown) onto a focal plane 1508. If a refractive pyramid sensor 1510a, 1510b and 1510c is placed at each focused spot, each pyramid sensor can create four beams, which can be re-imaged using a collimator (not shown) onto a detector 1512.

At this point, if the detector 1512 is positioned in the pupil plane, the deformation measured by the wavefront sensor is mainly the one coming from the first layer 1506 (which is, in the exemplary case of FIG. 15, very close to the entrance pupil of the system). In reality, how sensitive the sensor is to other layers with respect to the first layer 1506, is dependant on how far are these layers are from the first layer, and, particularly, on its depth of focus, which is related to the wavefront sensor Field of View (FoV). The larger the FoV (which means that the references shall be taken at a certain distance one from another) the smaller its depth of focus. Summarizing, if, for the example of FIG. 15, the need is to be very sensitive to a thin layer deformation, the selection of the references shall be done having a large FoV for the WFS. On the other hand, the references shall be selected closer if the need is to be sensitive to a deeper portion of the volume under examination.

The conjugation of the WFS to different portions of this volume involves focusing the detector. For example, considering FIG. 15, assume the second layer 1504 is conjugated to see its aberrations. The detector 1512 is moved (the exact amount of which depends on the optical system of course) in the direction of the focal plane 1508 (similar to what is done with a photographic objective when it is desired to focus to a different distance). Of course, in this case, the shape of the pupil on the detector changes and will reflect the position of the references used by the sensor, as shown in FIGS. 16A and 16B.

Figure 16A:
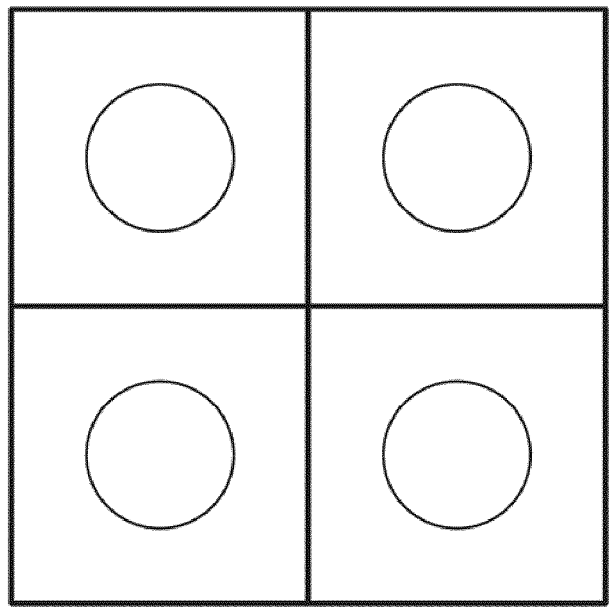
FIGS. 16A and 16B further illustrate optical co-additional of light using a layer orientated technique in accordance with one embodiment of the present invention.
Figure 16B:
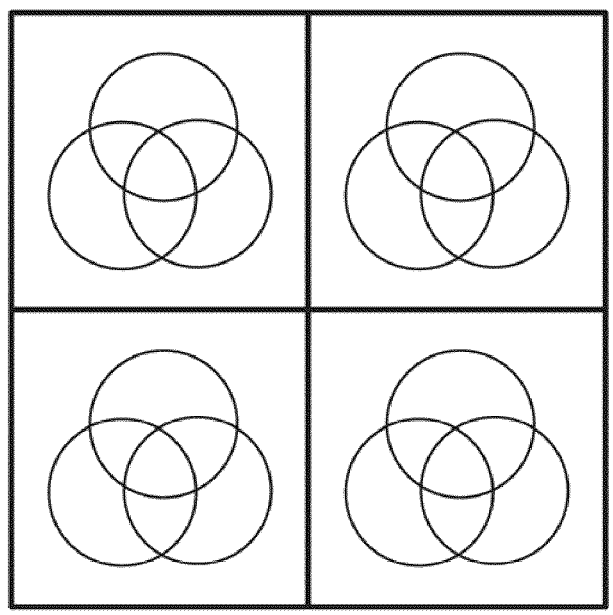

FIGS. 16A and 16B illustrate the optical co-addition of the light in the LO technique. In FIG. 16A, the wavefront sensor is conjugated to the entrance pupil of the system, where there is by definition superimposition of the light. In FIG. 16B, the sensor is conjugated to a different distance, where the light is not perfectly superimposed and the pupil is not regular, and normally takes the name of "meta-pupil".

Next, an optical layout based on concepts outlined in the paragraphs above (sinusoidal wavefront sensor and layer oriented approach) are described with reference to FIG. 17. First, in order to reach a high sensitivity of the sensor on the eye under examination, an optical system with a small depth of focus in the region of interest can be used (or stated differently, a system that allows the light beams to impinge on the eye pupil at large angles). This optical effect can be obtained by an eyepiece 1702 with a short focal length that provide high field angle; the entrance pupil of the eyepiece can be the pupil of the eye to be analyzed.

To create reference beacons on the retina 1704, it then suffices to image a certain number of super luminescent diode (SLD) or laser diode (LD) light sources on the intermediate image plane (IIP) 1708 of the eyepiece 1702. The eyepiece then acts as a collimating lens and the laser sources are focused on different positions 1710a, 1710b and 1710c on the retina 1704. The light reflected back from these points 1710a, 1710*b* and 1710*c* provide reference beacons for a wavefront sensor to analyze. Another advantage of using an eyepiece as a collimating lens is that it provides a compact multi-source optical system. Each beacon projected on the retina can be conjugated to a sinusoidal pattern plate by an optical relay lens system; another relay lens placed behind the sinusoidal plate projects the pupil of the optical system on a detector.

Figure 17:
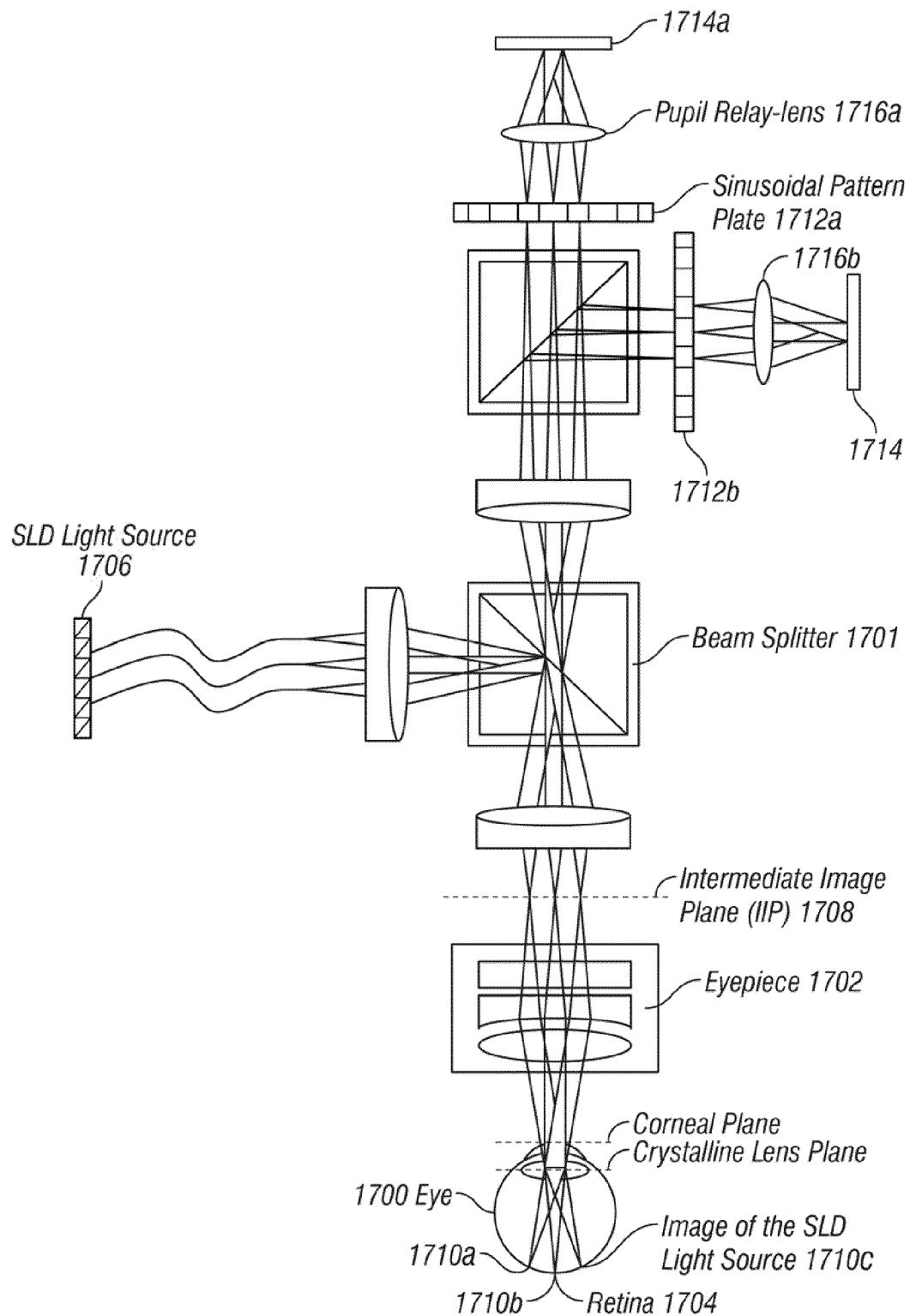
FIG. 17 is a schematic diagram of a lens prescription (.LPS) optical system in accordance with one embodiment of the present invention.

In the example of FIG. 17, light coming from light source 1706 is split via beam splitter 1701 and focused on intermediate image plane 1708 and then, via eye-piece 1702, on the retina 1704 of the eye. The resulting retina beacons are, in the example of FIG. 17, projected by a unit magnification lens system and beam splitter, onto two perpendicularly positioned sinusoidal pattern plates 1712*a* and 1712*b*. The pupil of the optical layout on each sinusoidal pattern plate is then relayed onto two CCD detectors 1714*a* and 1714*b*, one for each path.

Figure 18:
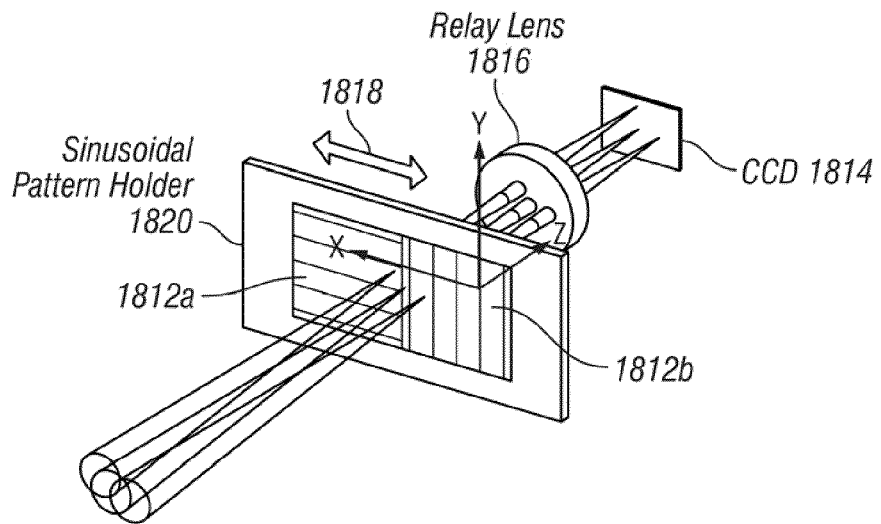
FIG. 18 is a schematic diagram of a lens prescription (LPS) optical system having two sinusoidal patterns on a single plate in accordance with one embodiment of the present invention.
Figure 19A:
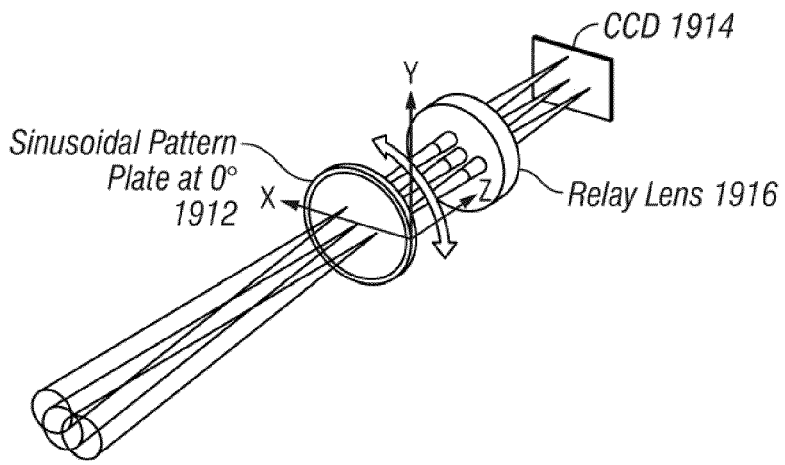
FIGS. 19A and 19B are schematic diagrams of a lens prescription (LPS) optical system having rotating sinusoidal pattern plate in accordance with one embodiment of the present invention.
Figure 19B:
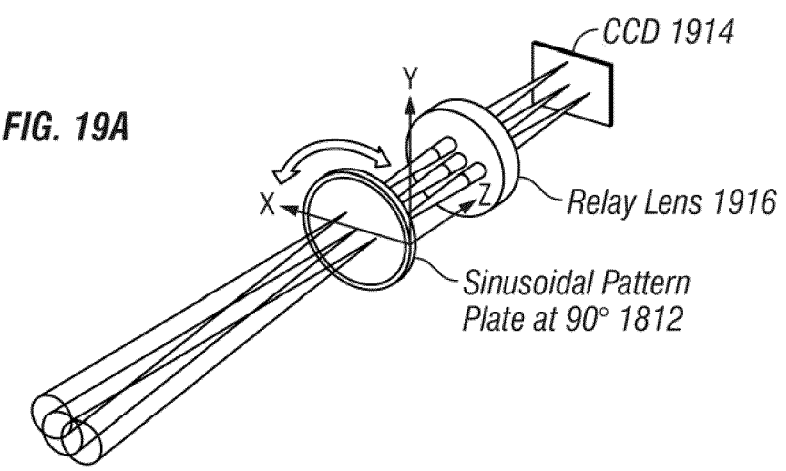
Figure 20:
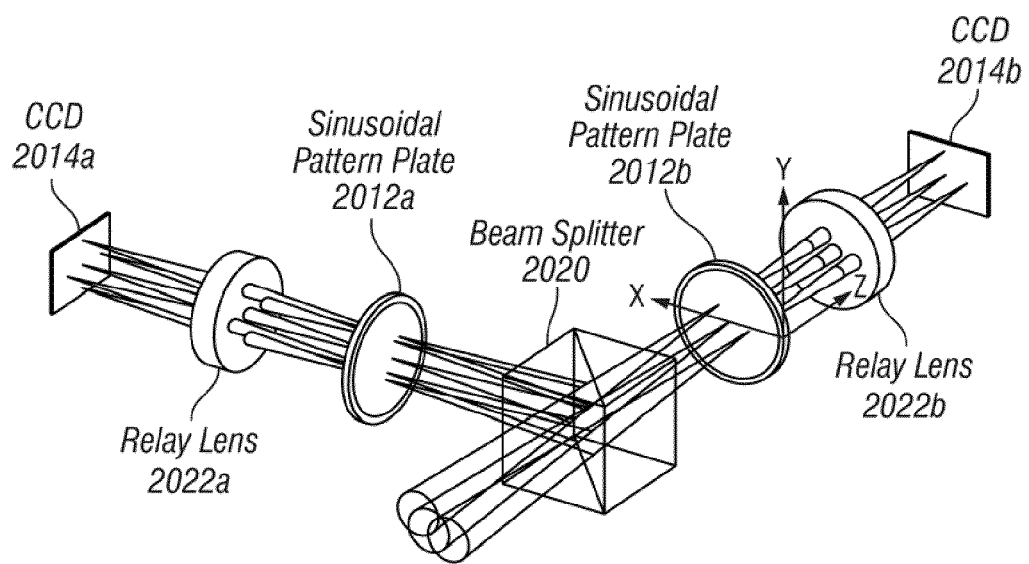
FIG. 20 is a schematic diagram of a lens prescription (LPS) optical system using two separate sinusoidal pattern plates in accordance with one embodiment of the present invention.

In accordance with one embodiment, each sinusoidal pattern is proportional to just one single first-derivative of the wavefront (the one which is orthogonal to the sine-pattern direction). But, wavefront pattern can also be constructed using derivatives in both directions (x and y). This may be accomplished in different ways, including the following:

a) As illustrated in FIG. 18, two adjacent sinusoidal pattern plates 1812*a* and 1812*b* can be shifted in orthogonal directions (as indicated by the arrow 1818 in FIG. 18). The reference beacons can be projected, first, on the first plate 1812*a* and then on the second plate 1812*b* by moving a plate holder 1820 holding the two plates.

b) With reference to FIG. 19, a similar result can be achieved by a single sinusoidal pattern plate 1912. Here, two images can be recorded corresponding to two derivatives. The first while the plate 1912 is in a first position (FIG. 19A), and a second after the plate has been rotated 90° (FIG. 19B) so that the pattern on plate 1912 in the first position is perpendicular to the pattern in the second position.

c) FIG. 20 depicts an arrangement similar to that illustrated in FIG. 17. Here, the projected image of the reference beacons can be split in two beams by beam splitter 2020. Each beam is then focused onto distinct sinusoidal plates 2012*a* and 2012*b*, whose patterns are perpendicular to one another.

If a different layer of the volume of an eye is to be examined, the detector (CCD) is moved to a corresponding position. For example, the detector can be moved further away or closer to the pupil relay lens, in such a way that it will be conjugated to the new layer to be examined.

In accordance with one embodiment, the light coming from several beacons overlaps optically onto one single detector, which is sensing a specific layer producing the wavefront deformation. In this way, only one single sinusoidal pattern and the CCD detector (or two if the first-derivatives in both directions are considered) is needed, and the light coming back from each beacon can be used in a more efficient way, being collected by a single CCD.

In use, the patient looks at a fixation target while the device self aligns or while the physician aligns it to the examined eye. Once the alignment process is completed, the acquisition starts, gathering both the wavefront components for layers of the eye and biometric data for each of the cornea and lens surfaces by use of an axial length meter. A measurement of the entire axial length of the eye can also be collected during this step.

The device may be used as a conventional wavefront analyzer or as a differential wavefront analyzer. In both cases, aberration maps can be generated. In the first use, related to the total aberration, and, in the second use, related to the aberration of the desired eye portion.

The acquired data can also be stored on a local or remote database for later processing.

Real-time Intra-operative Tester (RTT)

Figure 21A:
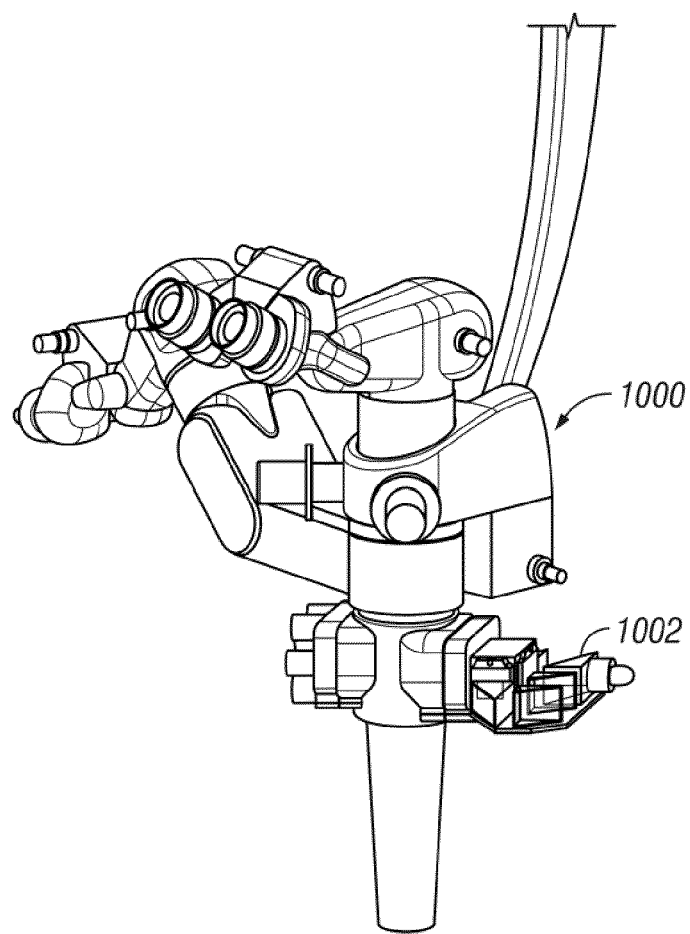
FIG. 21A illustrates a surgical microscope having a plug-in RTT module inserted therein according to one embodiment of the invention.
Figure 21B:
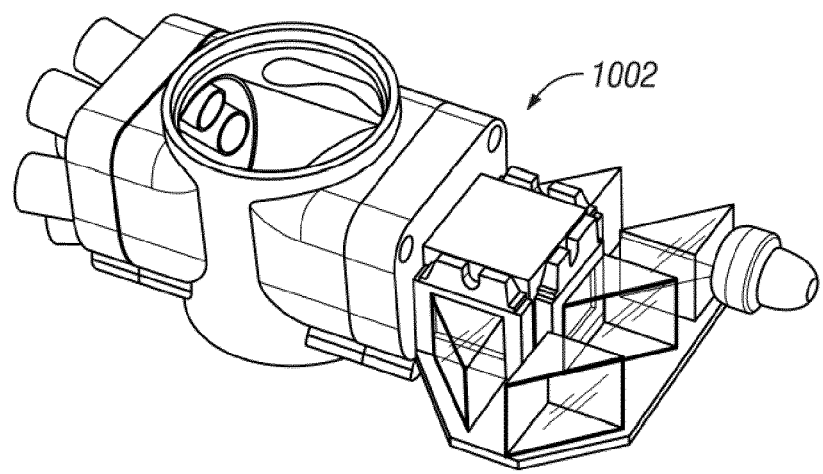
FIG. 21B is a perspective view of the RTT module of FIG. 10A taken away from the surgical microscope according to one embodiment of the invention.

An RTT can be used to assist a surgeon during a BIOL implantation process, in order to properly align and orient the BIOL and also to functionally test the BIOL after the implantation. FIG. 21A illustrates a surgical microscope 1000 with an RTT module 1002 inserted into a section of the surgical microscope 1000. FIG. 21B illustrates the RTT module 1002 removed from the surgical microscope 1000. In accordance with one embodiment, the RTT module 1002 is a plug-in device for a surgical microscope, such as microscope 1000.

The RTT module 1002 can comprise a wavefront analyzer, a topographer and a Purkinje image analyzer that detects refractive index variations between eye structures of the eye and determines their positions. The RTT module 1002 can be used to analyze a patient's eye in real time. As described in more detail with respect to FIG. 22, the RTT module 1002 can provide an overlaid view of a calculated map (both topographic and wavefront) through the microscope oculars and/or on a separate display, together with numerical data reporting IOL positioning inside the eye. The RTT module 1002 can also provide alignment indicators that help a surgeon to properly position the microscope objective in order to capture significant and accurate wavefront response from the eye under surgery.

Figure 22:
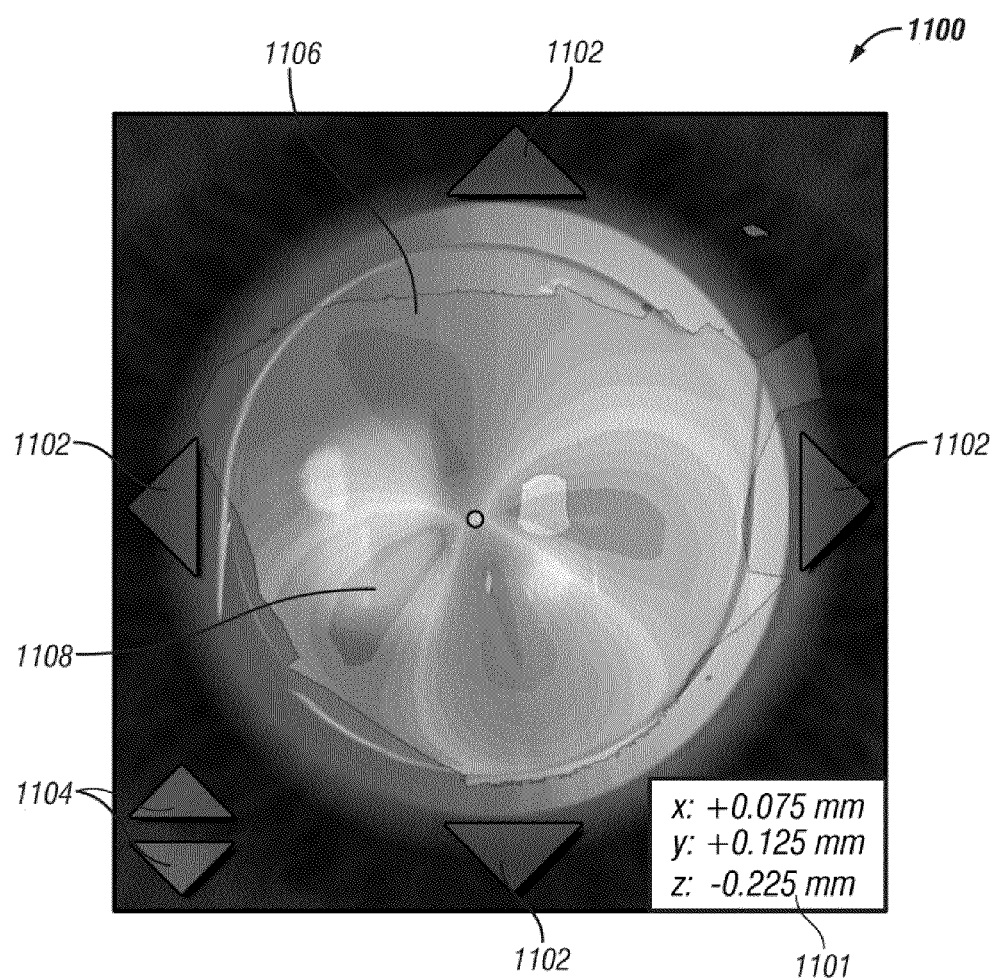
FIG. 22 illustrates an RTT overlay display according to one embodiment of the invention.

FIG. 22 is an exemplary view of an overlay display 1100 using the RTT module 1002, as viewed through the surgical microscope 1000 oculars. Display 1100 includes X/Y alignment indicators 1102 and focus/Z alignment indicators 1104. FIG. 22 illustrates implanted intraocular lens (IOL) 1106 partly overlaid by a topography or wavefront map 1108. In one embodiment, either a topography map or a wavefront map may be selected depending upon user preference. Alignment values 1110 are also displayed at one corner of the display 1100. In accordance with one embodiment, an indicator or value can be displayed in a first color (e.g., green) when the indicator or value is determined to be properly aligned or falls within a predetermined range, and in a second or a third color (e.g., red or yellow) when the indicator or value is determined to be out-of-alignment or outside the predetermined range.

One embodiment of the RTT can help a surgeon during an IOL implant surgery to correctly position the IOL either in an x or y rotation and estimate a final refractive error. Moreover, immediately after surgery, the RTT can be used to check the IOL positioning, estimate any corneal astigmatism, and estimate any residual refractive error. One embodiment of the RTT can also be used to estimate the corneal curvature during a Keratoplasty, allowing the surgeon to correct unwanted corneal shapes acting for example on the suturing wire tension.

As discussed above, an embodiment of the RTT is an instrument designed to co-operate real time with the surgeon, providing a complete set of information on the positioning of the IOL during the implantation and on the effectiveness of the curvatures of the IOL in correcting the functionalities of the replaced lens. Two different optical paths are integrated in the same device, to provide real time both information regarding any misalignments and tip-tilt of the IOL with respect to the correct position of the implant, and an evaluation of the aberrations of the eye with IOL as a whole.

In accordance with one embodiment, a sequence of information provided by RTT during the implantation is, first, information related to the actual position of an implanted IOL; more specifically information relating to any decentering and tip-tilt with respect to a correct implantation position of the IOL. Second, information for evaluating a level of optical correction introduced by the IOL; more specifically, how the curved surfaces of the IOL are cooperating with the index of the material of the IOL to compensate for refractive error of the patient's removed lens. In this manner, the RTT can have two optical layouts, each optical layout configured to gather the information discussed above.

Figure 23:
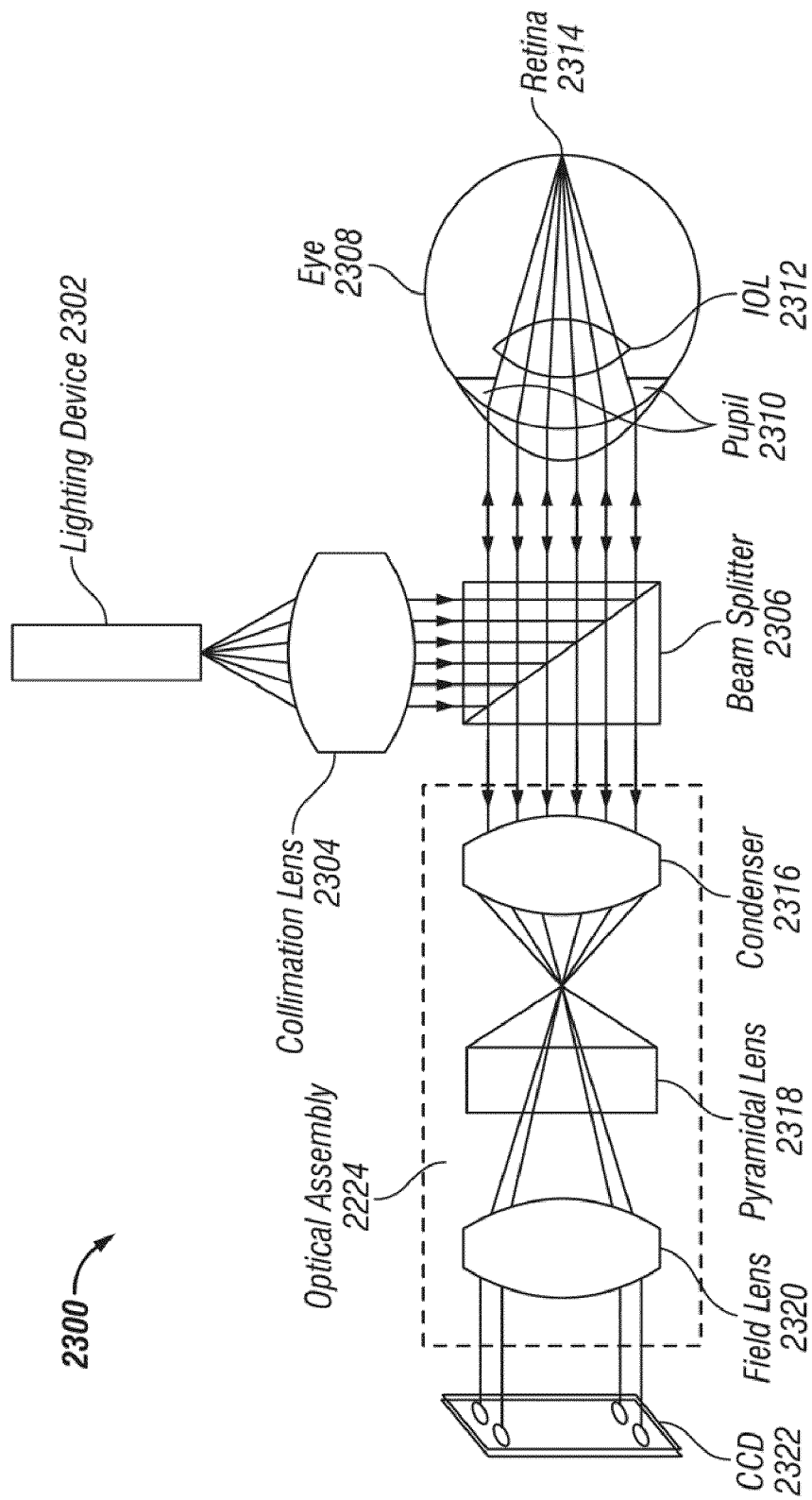
FIG. 23 illustrates a first optical layout of the RTT according to one embodiment of the invention.

A first optical layout 2300 of the RTT is illustrated in FIG. 23. The optical layout 2300 includes a lighting device 2302, which can include an LED source coupled with an optical fiber to irradiate a surface at or near a focal point of collimation lens 2304. The collimation lens 2304 then directs a light beam through beam splitter 2306, which redirects at least part of the beam into a patient's eye 2308, through pupil 2310, IOL 2312 and onto retina 2314. Light reflected from the eye 2308 then travels back through beam splitter 2306 and into an optical assembly 2224. The assembly 2224 is configured as a pyramid wavefront sensor. However, in other embodiments, the assembly can be configured as a different type of wavefront sensor, such as Shack-Hartman or Talbot-Moiré sensor.

Optical assembly 2224 is a pupil wavefront sensor and can include a condenser lens 2316, which is configured to focus an input beam light into a point positioned over a vertex of pyramidal lens 2318. Optical assembly 2224 also includes a field lens 2320, which redirects horizontally the four light beams generated by the pyramidal lens 2318.

A detector 2322 (e.g., CCD detector) can be positioned at the end of the optical path of layout 2300 for detecting the four images of the pupil 2310 projected onto the detector by the layout 2300. These four images can then be processed to obtain wavefront information as is known in conventional wavefront sensing using a pyramid.

Using an incremental ratio (R1, R2) of the summation of the intensities along two orthogonal axis of the detector 2322, a total power of the eye and the IOL as a whole can be calculated. The total power of the eye and the IOL can be calculated using the following equations, where variables A, B, C and D are the detected intensities of each of the four images projected onto the detector 2322, respectively:

$$\frac{dW}{dX} \approx \frac{(B+D)-(A+C)}{(A+B+C+D)}(R1); \quad \frac{dW}{dY} \approx \frac{(B+D)-(A+C)}{(A+B+C+D)}(R2);$$

In addition, optical aberrations of the implant can be calculated. For example, astigmatism can be calculated using Zernike polynomials using techniques well known by those of ordinary skill in the art.

Figure 24:
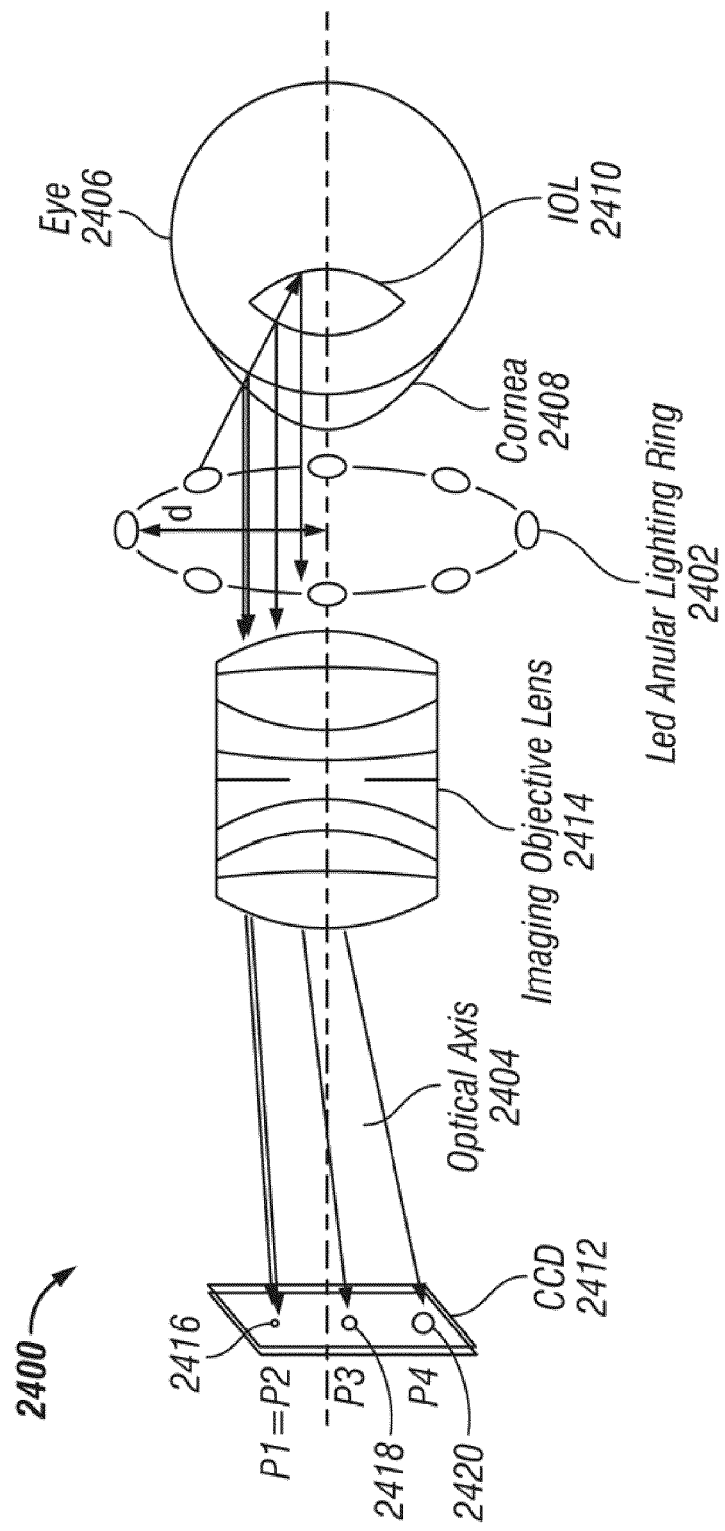
FIG. 24 illustrates a second optical layout of the RTT according to one embodiment of the invention.

A second optical layout 2400 of the RTT is illustrated in FIG. 24. Optical layout 2400 includes an LED annular lighting ring 2402, which emits tilted light rays with respect to the optical axis 2404 of an eye 2406 being examined. The rays emitted from annular ring 2402 are split into reflected and refracted components at each interface they encounter traveling through the eye 2406. For example, the interfaces can include the front and back surfaces of cornea 2408 and the front and back surfaces of the implanted IOL 2410. The reflected components of these rays are referred to as Purkinje images. In the example of FIG. 24, the Purkinje images are referenced as P1, P2, P3, P4, corresponding to the images reflected from the in and outer surfaces of the cornea 2408 and IOL, respectively.

Further to FIG. 24, the Purkinje P1, P2, P3, P4 are focalized on a detector 2412 (e.g., CCD detector) using an imaging objective lens 2414. In the example of FIG. 24, the P1 and P2 Purkinje images overlap on the detector 2412 at area 2416, image P2 is imaged on detector at area 2418 and image P3 is imaged on detector at area 2420. The information obtained from detector 2412 can then be used to calculate various parameters pertaining to the implanted IOL, including a rotation angle γ, an IOL tilt angle α, and an IOL decentering value δ.

In accordance with one embodiment, like components used in the first optical layout can also be used in the second optical layout. Thus, for example, detector 2322 in the first optical layout can also be used as detector 2412 in the second optical layout.

Locations of the P1, P3, P4 Purkinje images referenced to the pupil center can be estimated using the second optical layout. P1 is the Purkinje image obtained by the reflection of the light source (placed at a distance d from the optical axis) from the front corneal surface; while P3 and P4 are the images reflected from the front lens and back lens surfaces. As is known in the art, each set of Purkinje's images (P1,P3,P4) can be related to a rotation angle of the eye (γ) and tilt and decenter of the lens (α and δ, respectively) by a linear relationship (matrix A) whose parameters can be obtained by ray-tracing simulations. By using values for a rotation angle, tilt and decenter, and the measured Purkinjes (P1, P3, P4), the unknown parameters can be determined by inverting matrix A (i.e. V=A$^{-1}$P).

However, the matrix A is an approximation, which leads to approximate V values. A better approximation can be obtained by assuming that matrix A is also a function of the V parameters themselves. In other words, computing a different matrix A for each different eye configuration (global rotation angle, lens tilt and lens decenter) can obtain a better approximation.

This leads to an iterative procedure where matrix A is computed by the V values. At each successive iteration, inverting matrix A (i.e. V=A$^{-1}$P) obtains a closer approximation to the V values. The closeness is controlled by what is referred to herein as an epsilon star number; the smaller the value of epsilon star, the closer the approximation of the matrix A and, consequently the unknown values of V.

Figure 25:
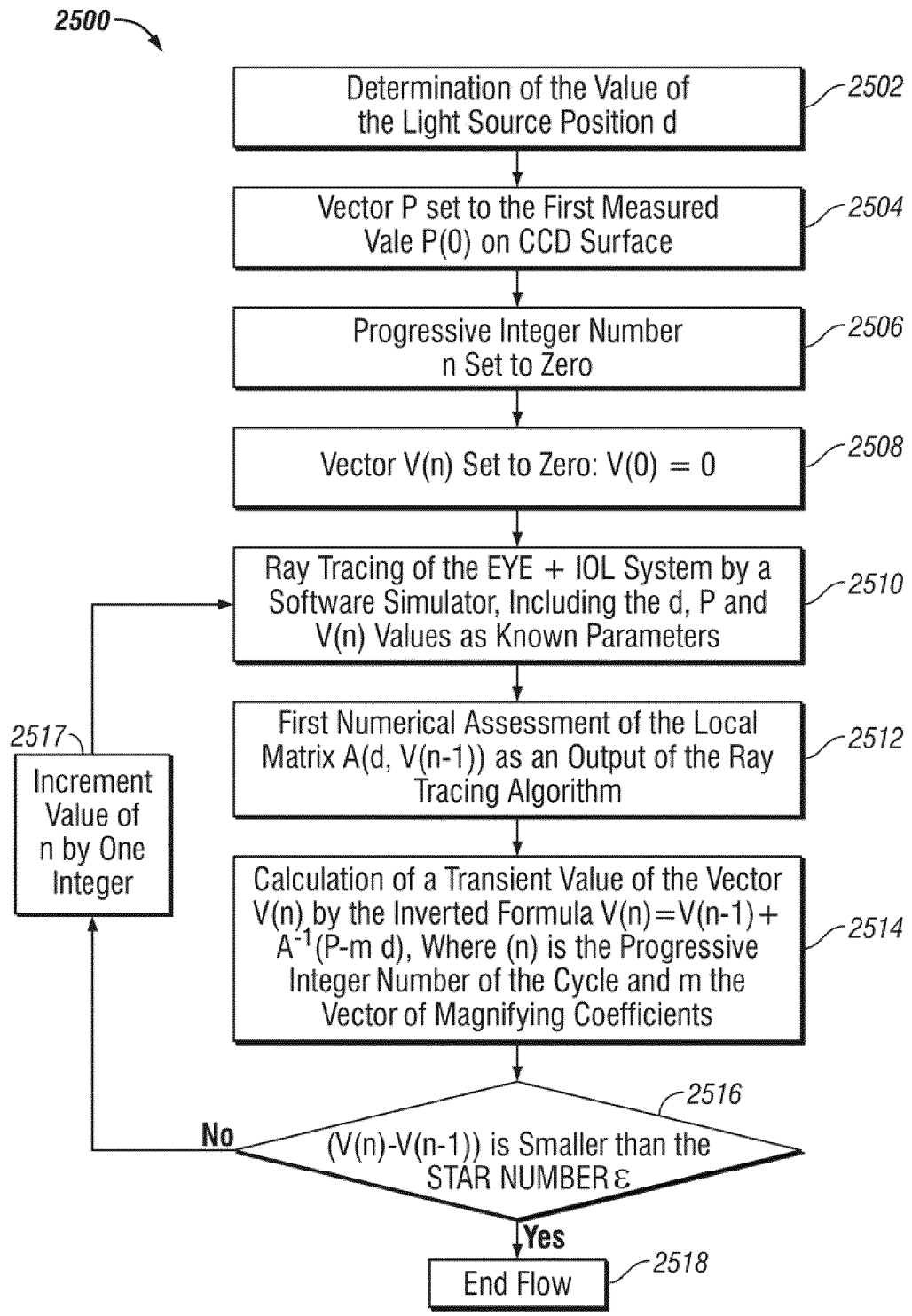
FIG. 25 is a flow chart of a process for calculating optical parameters using the RTT according to one embodiment of the invention.

FIG. 25 is a flowchart illustrating a process 2500 for calculating a rotation angle γ, an IOL tilt angle α, and an IOL decentering value δ using the RTT. At step 2502, a value for a distance d of the light source is determined. As illustrated in FIG. 24, the distance d can be a distance from the annular light ring 2402 to the optical axis 2404. Next, at step 2504, a vector P is set to a first measured value P(0) on detector. Vector P=(P1, P2, P3, P4), which components along the plane of the detector (x, y) are Px=(P1x, P2x, P3x, P4x) and Py=(P1y, P2y, P3y, P4y). Note that in the example of FIG. 24, P1 and P2 overlap due to their proximity. In such a case, only three Purkinje Images (P1) need by detected, wherein P1 and P2 are too close to be distinguished.

At step 2506, a progressive integer number n is set to zero. Accordingly, in step 2508, vector V(n) is set to zero, wherein V(0)=0. The process 2500 then ray traces the eye and IOL, using a software simulator in step 2510. In this step, the distance d, vector P and vector V(n) values are known parameters.

At step 2512, a numerical assessment is performed using a local matrix A(d, V(n−1)) as an output of the ray tracing algorithm. In one embodiment, the matrix is a 3×3 scalar element matrix, wherein the elements of the matrix are unknown at the starting point of the algorithm.

A transient value of the vector V(n) is then calculated at step 2514 using the following inverted formula: V(n)=V(n−

1)+Z$^{-1}$(P−m d), where (n) is the progressive integer number of the cycle and m is a vector of magnifying coefficients. At step, process 2500 determines whether (V(n)−V(n−1)) is less than a star number ϵ, where the star number is some predefined number less than 1, such as 0.001. If no, then the value of n is incremented by one integer in step 2517 and the process 2500 proceeds back to step 2510. However, if (V(n)−V(n−1)) determined to be less than the star number ϵ in step 2516, then the process ends at step 2518.

Thus, process 2500 is an iterative process that converges to a final solution. V(n) is constituted by the variables γ, α and δ, and these variables are used as inputs for the algorithm at every iteration. The variables are also the outputs of the algorithm. After a number of iterations, the difference between the V(n−1) vector value and the new computed V(n) vector value will be less than the star number, indicating that a convergence point has been reached for the algorithm. The final value of all the components of the vector V(n) are then the values for γ, α and δ.

It can be noted that one or more steps of the processes described herein can be performed by instructions in the form of computer-readable residing in memory of a computer. Note that instructions can be stored and transported on any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any medium that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random access memory (RAM) (magnetic), a read-only memory (ROM) (magnetic), an erasable programmable read-only memory (EPROM) (magnetic), an optical fiber (optical), portable optical disc such a CD, CD-R, CD-RW, DVD, DVD-R, or DVD-RW, or flash memory such as compact flash cards, secured digital cards, USB memory devices, memory stick, etc. Note that the computer-readable medium could even be paper or another suitable medium upon which the program is printed, as the program text can be electronically captured via optical scanning of the paper or other medium, then compiled, interpreted or otherwise processed in a suitable manner if necessary, and then stored in a computer memory.

As user herein, the term "module" refers to any unit or combination of units incorporating software, firmware, hardware, or any combination thereof that is designed and configured to perform a desired function. In addition, the term "module" does not imply that the components or functionality described or claimed as part of the module are all configured in a common package. Indeed, any or all of the various components of a module, whether control logic or other components, can be combined in a single package or separately maintained and can further be distributed across multiple locations.

While this invention has been described in terms of several preferred embodiments, there are alterations, permutations, and equivalents, which fall within the scope of this invention. For example, the term "computer" does not necessarily mean any particular kind of device, combination of hardware and/or software, nor should it be considered restricted to either a multi purpose or single purpose device.

Although the present invention has been fully described in connection with embodiments thereof with reference to the accompanying drawings, it is to be noted that various changes and modifications will become apparent to those skilled in the art. Such changes and modifications are to be understood as being included within the scope of the present invention as defined by the appended claims.

We claim:

1. A customized IOL, comprising:
    (a) an optic disc configured to correct at least one optical aberration of a patient's eye; and
    (b) one or more parametric haptics extending from an outer circumference of the optic disc, the one or more haptics configured to maintain the IOL in a pre-calculated position within a patient's eye.

2. The customized IOL of claim 1, wherein the IOL is configured to be positioned inside a capsular bag of a patient's eye, with an optical axis of the optic disc aligned with the iris aperture of the eye so that light entering through the iris aperture is focused at a focal point on the eye's retina.

3. The customized IOL of claim 1, wherein a visual center of the optic disc is decentered from a geometric center of the IOL.

4. The customized IOL of claim 1, comprising a plurality of haptics.

5. The customized IOL of claim 4, wherein at least one of the plurality of haptics has a different shape than at least one of the other plurality of haptics.

6. The customized IOL of claim 4, wherein at least one of the plurality of haptics has a different length than one of the other plurality of haptics.

* * * * *